US010617711B2

(12) United States Patent
Smejkalova et al.

(10) Patent No.: US 10,617,711 B2
(45) **Date of Patent: *Apr. 14, 2020**

(54) ANTITUMOR COMPOSITION BASED ON HYALURONIC ACID AND INORGANIC NANOPARTICLES, METHOD OF PREPARATION THEREOF AND USE THEREOF

(71) Applicant: CONTIPRO PHARMA A.S., Dolní Dobrouc (CZ)

(72) Inventors: Daniela Smejkalova, Pisek (CZ); Kristina Nesporova, Brno (CZ); Martina Tepla, Policka (CZ); Jakub Syrovatka, Letohrad (CZ); Gloria Huerta-Angeles, Ceska Trebova (CZ); Martina Pospisilova, Olomouc (CZ); Vit Matuska, Ostrava-Poruba (CZ); Jiri Mrazek, Zamberk (CZ); Andrea Galisova, Rybany (SK); Daniel Jirak, Jesenice (CZ); Vladimir Velebny, Zamberk (CZ)

(73) Assignee: Contipro a.s., Dolni Dobrouc (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/322,776

(22) PCT Filed: Jun. 30, 2015

(86) PCT No.: PCT/CZ2015/000068

§ 371 (c)(1),
(2) Date: Dec. 29, 2016

(87) PCT Pub. No.: WO2016/000669

PCT Pub. Date: Jan. 7, 2016

(65) Prior Publication Data

US 2017/0143756 A1 May 25, 2017

(30) Foreign Application Priority Data

Jun. 30, 2014 (CZ) ................................ PV2014451

(51) Int. Cl.

| | |
|---|---|
| ***A61K 31/728*** | (2006.01) |
| ***A61K 9/00*** | (2006.01) |
| ***A61P 35/00*** | (2006.01) |
| ***A61K 47/36*** | (2006.01) |
| ***A61K 9/107*** | (2006.01) |
| ***A61K 33/26*** | (2006.01) |
| ***A61K 33/30*** | (2006.01) |
| ***A61K 49/18*** | (2006.01) |
| ***A61K 9/51*** | (2006.01) |
| ***A61K 31/337*** | (2006.01) |
| ***A61K 41/00*** | (2020.01) |
| ***A61K 45/06*** | (2006.01) |
| ***A61K 47/02*** | (2006.01) |
| ***A61K 49/12*** | (2006.01) |
| ***C08B 37/08*** | (2006.01) |

(52) U.S. Cl.

CPC .......... *A61K 31/728* (2013.01); *A61K 9/0019* (2013.01); *A61K 9/1075* (2013.01); *A61K 9/5115* (2013.01); *A61K 9/5123* (2013.01); *A61K 31/337* (2013.01); *A61K 33/26* (2013.01); *A61K 33/30* (2013.01); *A61K 41/0057* (2013.01); *A61K 45/06* (2013.01); *A61K 47/02* (2013.01); *A61K 47/36* (2013.01); *A61K 49/12* (2013.01); *A61K 49/1809* (2013.01); *A61K 49/1839* (2013.01); *A61K 49/1887* (2013.01); *C08B 37/0072* (2013.01)

(58) Field of Classification Search

None

See application file for complete search history.

(56) References Cited

U.S. PATENT DOCUMENTS

| | | | |
|---|---|---|---|
| 3,075,527 | A | 1/1963 | Bechtold |
| 3,720,662 | A | 3/1973 | Tessler et al. |
| 3,728,223 | A | 4/1973 | Kaneko et al. |
| 4,043,331 | A | 8/1977 | Martin et al. |
| 4,205,025 | A | 5/1980 | Hart et al. |

(Continued)

FOREIGN PATENT DOCUMENTS

| | | | |
|---|---|---|---|
| CA | 2512730 | A1 | 7/2004 |
| CH | 628088 | A5 | 2/1982 |

(Continued)

OTHER PUBLICATIONS

Cayman Chemical, Stearic Acid, obtained online at: https://www.caymanchem.com/pdfs/10011298.pdf, p. 1. (Year: 2017).*

(Continued)

*Primary Examiner* — Abigail Vanhorn
(74) *Attorney, Agent, or Firm* — Wood Herron & Evans LLP

(57) ABSTRACT

The invention relates to an antitumor composition based on hydrophobized hyaluronan and inorganic nanoparticles stabilized by oleic acid. The hydrophobized hyaluronan in the form of an acylated hyaluronan serves in the composition as a carrier of inorganic nanoparticles. Out of the group of inorganic nanoparticles, the composition may comprise superparamagnetic nanoparticles, nanoparticles of ZnO and moreover, upconversion nanoparticles. Said composition is selectively cytotoxic with respect to both suspension and adherent tumor cell lines, especially with respect to tumor cell lines of colorectum carcinoma and adenocarcinoma, lung carcinoma, hepatocellular carcinoma and breast adenocarcinoma. The highest cytotoxic effects were observed in case of the composition based on an oleyl derivative of hyaluronan with SPIONs. The composition of acylated hyaluronan with SPIONs may also be advantageously used for an in vivo detection of accumulation of the composition in the body, preferably in a tumor or in liver. Said composition is sterilizable in the final package.

21 Claims, 26 Drawing Sheets

(56) References Cited

U.S. PATENT DOCUMENTS

| | | | | |
|---|---|---|---|---|
| 4,258,134 | A | 3/1981 | Yoshida et al. | |
| 4,713,448 | A | 12/1987 | Balazs et al. | |
| 4,761,401 | A | 8/1988 | Couchman et al. | |
| 4,851,521 | A | 7/1989 | Della Valle et al. | |
| 4,965,353 | A | 10/1990 | Della Valle et al. | |
| 5,455,349 | A | 10/1995 | Grasshoff et al. | |
| 5,462,976 | A | 10/1995 | Matsuda et al. | |
| 5,520,916 | A | 5/1996 | Dorigatti et al. | |
| 5,522,879 | A | 6/1996 | Scopelianos | |
| 5,523,093 | A | 6/1996 | Della Valle et al. | |
| 5,550,225 | A | 8/1996 | Philippe | |
| 5,616,568 | A | 4/1997 | Pouyani et al. | |
| 5,658,582 | A | 8/1997 | Dorigatti et al. | |
| 5,676,964 | A | 10/1997 | Della Valle et al. | |
| 5,690,961 | A | 11/1997 | Nguyen | |
| 5,824,335 | A | 10/1998 | Dorigatti et al. | |
| 5,868,973 | A | 2/1999 | Muller et al. | |
| 6,025,444 | A | 2/2000 | Waki et al. | |
| 6,075,066 | A | 6/2000 | Matsuda et al. | |
| 6,162,537 | A | 12/2000 | Martin et al. | |
| 6,207,134 | B1* | 3/2001 | Fahlvik | A61K 49/1854 424/9.322 |
| 6,288,043 | B1 | 9/2001 | Spiro et al. | |
| 6,509,039 | B1 | 1/2003 | Nies | |
| 6,613,897 | B1 | 9/2003 | Yatsuka et al. | |
| 6,632,802 | B2 | 10/2003 | Bellini et al. | |
| 6,641,798 | B2 | 11/2003 | Achilefu et al. | |
| 6,673,919 | B2 | 1/2004 | Yui et al. | |
| 6,683,064 | B2 | 1/2004 | Thompson et al. | |
| 6,719,986 | B1 | 4/2004 | Wohlrab et al. | |
| 6,902,548 | B1 | 6/2005 | Schuler et al. | |
| 6,953,784 | B2 | 10/2005 | Thompson et al. | |
| 7,125,860 | B1 | 10/2006 | Renier et al. | |
| 7,214,759 | B2 | 5/2007 | Pacetti et al. | |
| 7,345,117 | B1 | 3/2008 | Barbucci et al. | |
| 7,550,136 | B2 | 6/2009 | Warner et al. | |
| 7,680,038 | B1 | 3/2010 | Gourlay | |
| 7,951,936 | B2 | 5/2011 | Sato | |
| 8,062,654 | B2 | 11/2011 | Nelson et al. | |
| 8,129,449 | B2 | 3/2012 | Heinzman et al. | |
| 8,143,391 | B2 | 3/2012 | Yasugi et al. | |
| 8,247,546 | B2 | 8/2012 | Stucchi et al. | |
| 9,017,725 | B2 | 4/2015 | Mitra et al. | |
| 9,492,586 | B2 | 11/2016 | Wolfova et al. | |
| 9,522,966 | B2 | 12/2016 | Buffa et al. | |
| 2002/0016472 | A1 | 2/2002 | Tsien et al. | |
| 2002/0026039 | A1 | 2/2002 | Bellini et al. | |
| 2002/0076810 | A1 | 6/2002 | Radice et al. | |
| 2003/0113354 | A1 | 6/2003 | Schmid et al. | |
| 2003/0163073 | A1 | 8/2003 | Effing et al. | |
| 2003/0205839 | A1 | 11/2003 | Bachrach | |
| 2004/0101546 | A1 | 5/2004 | Gorman et al. | |
| 2004/0192643 | A1 | 9/2004 | Pressato et al. | |
| 2005/0112349 | A1 | 5/2005 | Laurencin et al. | |
| 2005/0118231 | A1 | 6/2005 | El Meski et al. | |
| 2005/0119219 | A1 | 6/2005 | Bellini et al. | |
| 2005/0126338 | A1 | 6/2005 | Yadav | |
| 2005/0266546 | A1 | 12/2005 | Warner et al. | |
| 2006/0046590 | A1 | 3/2006 | Chu et al. | |
| 2006/0084759 | A1 | 4/2006 | Calabro et al. | |
| 2006/0188578 | A1 | 8/2006 | Fernandez et al. | |
| 2006/0189516 | A1 | 8/2006 | Yang et al. | |
| 2006/0216324 | A1 | 9/2006 | Stucke et al. | |
| 2006/0281912 | A1 | 12/2006 | James et al. | |
| 2007/0149441 | A1 | 6/2007 | Aeschlimann et al. | |
| 2007/0202084 | A1 | 8/2007 | Sadozai et al. | |
| 2008/0009630 | A1 | 1/2008 | Gao et al. | |
| 2008/0063617 | A1 | 3/2008 | Abrahams et al. | |
| 2008/0071001 | A1 | 3/2008 | Sato | |
| 2008/0124395 | A1 | 5/2008 | Chen et al. | |
| 2008/0286300 | A1 | 11/2008 | Bardotti et al. | |
| 2009/0024019 | A1* | 1/2009 | Stein | G01N 33/54326 600/409 |
| 2009/0028788 | A1 | 1/2009 | Achilefu | |
| 2009/0180966 | A1* | 7/2009 | Borbely | A61K 31/519 424/9.36 |
| 2009/0252810 | A1 | 10/2009 | Tommeraas et al. | |
| 2010/0002155 | A1 | 1/2010 | Yamaguchi et al. | |
| 2010/0172892 | A1 | 7/2010 | Uvarkina et al. | |
| 2010/0207078 | A1 | 8/2010 | Marder et al. | |
| 2010/0247908 | A1 | 9/2010 | Velev et al. | |
| 2010/0310631 | A1 | 12/2010 | Domard et al. | |
| 2010/0310853 | A1 | 12/2010 | Schwiegk et al. | |
| 2010/0316682 | A1 | 12/2010 | Chen et al. | |
| 2011/0020917 | A1 | 1/2011 | Wen et al. | |
| 2011/0028062 | A1 | 2/2011 | Chester et al. | |
| 2011/0104070 | A1 | 5/2011 | Kang et al. | |
| 2011/0111012 | A1 | 5/2011 | Pepper et al. | |
| 2011/0196328 | A1 | 8/2011 | Bellini et al. | |
| 2011/0200676 | A1 | 8/2011 | Lin et al. | |
| 2011/0218331 | A1 | 9/2011 | Buffa et al. | |
| 2011/0229551 | A1 | 9/2011 | Doshi et al. | |
| 2011/0263724 | A1 | 10/2011 | Gurtner et al. | |
| 2012/0040463 | A1 | 2/2012 | Domard et al. | |
| 2012/0095205 | A1 | 4/2012 | Buffa et al. | |
| 2012/0245323 | A1 | 9/2012 | Buffa et al. | |
| 2012/0264913 | A1 | 10/2012 | Buffa et al. | |
| 2012/0277416 | A1 | 11/2012 | Carter et al. | |
| 2012/0289478 | A1 | 11/2012 | Rovati | |
| 2013/0017367 | A1 | 1/2013 | Ravagnan et al. | |
| 2013/0136784 | A1 | 5/2013 | Staab | |
| 2013/0195791 | A1 | 8/2013 | Berkland et al. | |
| 2013/0309706 | A1 | 11/2013 | Kruglick | |
| 2014/0120069 | A1 | 5/2014 | Huerta-Angeles et al. | |
| 2014/0242145 | A1 | 8/2014 | Yoo et al. | |
| 2015/0157463 | A1 | 6/2015 | Stad et al. | |
| 2015/0320873 | A1* | 11/2015 | Smejkalova | A61K 47/36 424/401 |

FOREIGN PATENT DOCUMENTS

| | | | | |
|---|---|---|---|---|
| CN | 101897976 | A | | 12/2010 |
| CN | 102154738 | A | | 8/2011 |
| CN | 103505736 | A | * | 1/2014 |
| CN | 103789874 | A | | 5/2014 |
| CZ | 2006605 | A3 | | 4/2008 |
| CZ | 20070299 | A3 | | 2/2009 |
| CZ | 301899 | B6 | | 7/2010 |
| CZ | 302503 | B6 | | 6/2011 |
| CZ | 302504 | B6 | | 6/2011 |
| CZ | 302856 | B6 | | 12/2011 |
| CZ | 302994 | B6 | | 2/2012 |
| CZ | 20101001 | A3 | | 2/2012 |
| CZ | 303879 | B6 | | 6/2013 |
| CZ | 304072 | B6 | | 9/2013 |
| CZ | 304266 | B6 | | 2/2014 |
| CZ | 304303 | B6 | | 2/2014 |
| CZ | 20120537 | A3 | | 3/2014 |
| CZ | 304512 | B6 | | 6/2014 |
| CZ | 305153 | B6 | | 5/2015 |
| DE | 10331342 | A1 | | 2/2005 |
| EP | 0161887 | A2 | | 11/1985 |
| EP | 0216453 | A2 | | 4/1987 |
| EP | 0763754 | A2 | | 3/1997 |
| EP | 0554898 | B1 | | 5/1997 |
| EP | 1369441 | A1 | | 12/2003 |
| EP | 1454913 | A1 | | 9/2004 |
| EP | 1115433 | B1 | | 12/2004 |
| EP | 1538166 | A1 | | 6/2005 |
| EP | 1217008 | B1 | | 3/2006 |
| EP | 1826274 | A1 | | 8/2007 |
| EP | 1905456 | A1 | | 4/2008 |
| EP | 1607405 | B1 | | 5/2011 |
| EP | 2399940 | A2 | | 12/2011 |
| EP | 2522337 | A2 | | 11/2012 |
| EP | 2899214 | A1 | | 7/2015 |
| JP | 62104579 | A | | 5/1987 |
| JP | 63044883 | A | | 11/1988 |
| JP | H0214019 | A | | 1/1990 |
| JP | H0347801 | A | | 2/1991 |
| JP | 06025306 | A | | 2/1994 |
| JP | H0625306 | A | | 2/1994 |
| JP | 3308742 | B2 | | 7/2002 |
| JP | 2004507586 | A | | 3/2004 |
| JP | 2004123785 | A | | 4/2004 |
| JP | 2007262595 | A | | 10/2007 |

(56) References Cited

FOREIGN PATENT DOCUMENTS

| | | | |
|---|---|---|---|
| JP | 3975267 | B2 | 12/2007 |
| JP | 2008208480 | A | 9/2008 |
| JP | 2008295885 | A | 12/2008 |
| JP | 2010138276 | A | 6/2010 |
| KR | 20070118730 | A | 12/2007 |
| KR | 20080062092 | A | 7/2008 |
| KR | 20080111815 | A | 12/2008 |
| KR | 20120118681 | A | 10/2012 |
| KR | 20130085294 | A | 7/2013 |
| NL | 9700003 | A | 7/1997 |
| WO | 199311803 | A1 | 6/1993 |
| WO | 199627615 | A1 | 9/1996 |
| WO | 9637519 | A1 | 11/1996 |
| WO | 1996035720 | A1 | 11/1996 |
| WO | 199808876 | A1 | 3/1998 |
| WO | 199901143 | A1 | 1/1999 |
| WO | 199957158 | A1 | 11/1999 |
| WO | 0063470 | A1 | 10/2000 |
| WO | 0134657 | A1 | 5/2001 |
| WO | 0218448 | A2 | 3/2002 |
| WO | 0218450 | A1 | 3/2002 |
| WO | 0232913 | A1 | 4/2002 |
| WO | 2002032285 | A2 | 4/2002 |
| WO | 0248197 | A1 | 6/2002 |
| WO | 02057210 | A1 | 7/2002 |
| WO | 2004061171 | A2 | 7/2004 |
| WO | 2005028632 | A2 | 3/2005 |
| WO | 2005092390 | A2 | 10/2005 |
| WO | 2005092929 | A1 | 10/2005 |
| WO | 2006010066 | A2 | 1/2006 |
| WO | 2006026104 | A2 | 3/2006 |
| WO | 2006056204 | A1 | 6/2006 |
| WO | 2006102374 | A2 | 9/2006 |
| WO | 2007003905 | A1 | 1/2007 |
| WO | 2007006403 | A2 | 1/2007 |
| WO | 2007009728 | A2 | 1/2007 |
| WO | 2007033677 | A1 | 3/2007 |
| WO | 2007101243 | A1 | 9/2007 |
| WO | 2008014787 | A1 | 2/2008 |
| WO | 2008031525 | A1 | 3/2008 |
| WO | 2008077172 | A2 | 7/2008 |
| WO | 2008115799 | A1 | 9/2008 |
| WO | 2009037566 | A2 | 3/2009 |
| WO | 2009050389 | A2 | 4/2009 |
| WO | 2009108100 | A1 | 9/2009 |
| WO | 2009148405 | A1 | 12/2009 |
| WO | 2010018324 | A1 | 2/2010 |
| WO | 2010028025 | A1 | 3/2010 |
| WO | 2010051783 | A1 | 5/2010 |
| WO | 2010061005 | A1 | 6/2010 |
| WO | 2010095049 | A1 | 8/2010 |
| WO | 2010095052 | A2 | 8/2010 |
| WO | 2010095056 | A2 | 8/2010 |
| WO | 2010105582 | A1 | 9/2010 |
| WO | 2010130810 | A1 | 11/2010 |
| WO | 2010138074 | A1 | 12/2010 |
| WO | 2011014432 | A1 | 2/2011 |
| WO | 2011028031 | A2 | 3/2011 |
| WO | 2011059325 | A2 | 5/2011 |
| WO | 2011059326 | A2 | 5/2011 |
| WO | 2011069474 | A2 | 6/2011 |
| WO | 2011069475 | A2 | 6/2011 |
| WO | 2012034544 | A2 | 3/2012 |
| WO | 2012089179 | A1 | 7/2012 |
| WO | 2012146218 | A1 | 11/2012 |
| WO | 2013056312 | A1 | 4/2013 |
| WO | 2013159757 | A1 | 10/2013 |
| WO | 2013167098 | A2 | 11/2013 |
| WO | 2013171764 | A2 | 11/2013 |
| WO | 2014023272 | A1 | 2/2014 |
| WO | 2014082608 | A1 | 6/2014 |
| WO | 2014082609 | A1 | 6/2014 |
| WO | 2014082611 | A1 | 6/2014 |

OTHER PUBLICATIONS

Office Action in U.S. Appl. No. 14/395,575, dated Jul. 6, 2017, 9 pgs.

Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.

Juhlin, L., "Hyaluronan in skin," Journal of Internal Medicine (1997) 242:61-66.

Kalyanaraman, B. et al., "Peroxidatic oxidation of catecholamines. A kinetic electron spin resonance investigation using the spin stabilization approach" Journal of Biological Chemistry (1984) 259(12) 7584-7589.

Katritzky, A.R. et al., "Cycloaddition Reactions of Heteroaromatic Six-Membered Rings," Chem. Rev. (1989) 89:827-861.

Kawaguchi, Y. et al., "The relation between the adsorption behavior at the interface and the conformational changes in hyaluronates partially modified with various acyl chains," Carbohydrate Polymers (1995) 26:149-154.

Kedar, U. et al., "Advances in polymeric micelles for drug delivery and tumor targeting," Nanomedicine: Nanotechnology, Biology, and Medicine (2010) 6(6):714-729.

Kim, B. et al., "Complexation Phenomena in pH-Responsive Copolymer Networks with Pendent Saccarides," Macromol. (2002) 35:9545-9550.

Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.

Korsmeyer, R.W. et al., "Mechanisms of solute release from porous hydrophilic polymers," International Journal of Pharmaceutics (1983) 15:25-35.

Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.

Kuo, J.W., "Practical Aspects of Hyaluronan Based Medical Products," 2006, CRC Press, Taylor & Francis Group, pp. 60-61.

Lapcik, L. Jr. et al., Chemicke Listy vol. 85, 1991, pp. 281-298.

Laurent, S. et al., "Magnetic fluid hyperthennia: Focus on superparamagnetic iron oxide nanoparticles," Advances in Colloid and Interface Science (2011) 166:8-23.

Leach, J.B. et al., "Characterization of protein release from photocrosslinkable hyaluronic acid-polyethylene glycol hydrogel tissue engineering scaffolds," Biomaterials (2005) 26:125-135.

Leach, J.B. et al., "Photocrosslinked Hyaluronic Acid Hydrogels: Natural, Biodegradable Tissue Engineering Scaffolds," Biotechnol Bioeng. (2003) 82:578-589.

Lee, Dong-Eun et al., "Amphiphilic hyaluronic acid-based nanoparticles for tumor-specific optical/MR dual imaging," Journal of Materials Chemistry (2012) 22(1):10444-10447.

Lee, F. et al., "An injectable enzymatically crosslinked hyaluronic acid-tyramine hydrogel system with independent tuning of mechanical strength and gelation rate," Soft Matter (2008) 4:880-887.

Lee, F. et al., "An injectable hyaluronic acid-tyramine hydrogel system for protein delivery," Journal of Controlled Release (2009) 134:186-193.

Lee, K.Y. et al., "Electrospinning of polysaccharides for regenerative medicine," Advanced Drug Delivery Reviews (2009) 61:1020-1032.

Lee, S.A. et al., "Spectroscopic studies of the physical properties of hyaluronate films: the origin of the phase transition," Carbohydrate Polymers (1995) 28:61-67.

Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.

Li, J. et al., "Electrospinning of Hyaluronic Acid (HA) and HA/Gelatin Blends," Macromolecular Rapid Communications (2006) 27:114-120.

(56) References Cited

OTHER PUBLICATIONS

Li, J. et al., "Redox-sensitive micelles self-assembled from amphiphilic hyaluronic acid-deoxycholic acid conjugates for targeted intracellular delivery of paclitaxel," Biomaterials (2012) 33(7):2310-2320.
Li, M. et al., Comparison of Two Ultrasmall Superparamagnetic Iron Oxides on Cytotoxicity and MR Imaging of Tumors, Theranostics (2012) 2(1):76-85.
Linhardt, R.J. et al., "Polysaccharide Lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials (2005) 26(23):4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.
Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E., "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Merriam Webster Online Dictionary, obtained online at: http://www.merriam-webster.com/cgi-bin/dictionary?book=Dictionary&va=derivative, downloaded on Jul. 5, 2008.
Milas, M. et al., "Characterization and Properties of Hyaluronic Acid (Hyaluronan)," Polysaccharides: Structural Diversity and Functional Versatility, by S. Dumitriu 1998, Marcel Dekker Inc., pp. 535-549.
Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Office Action in U.S. Appl. No. 14/113,527, dated Sep. 8, 2016, 10 pgs.
Office Action in U.S. Appl. No. 14/420,012, dated Jun. 16, 2016, 6 pgs.
Veitch, N.C., "Horseradish peroxidase: a modem view of a classic enzyme," Phytochemistry (2004) 65:249-259.
Wang, J. et al., "Polymeric Micelles for Delivery of Poorly Soluble Drugs: Preparation and Anticancer Activity In Vitro of Paclitaxel Incorporated into Mixed Micelles Based on Poly(ethylene Glycol)-Lipid Conjugate and Positively Charged Lipids," Journal of Drug Targeting (2005) 13(1):73-80.
Wang, X. et al., "Formation of water-resistant hyaluronic acid nanofibers by blowing-assisted electro-spinning and non-toxic post treatments," Polymer (2005) 46:4853-4867.
Weng, L. et al., "In vitro and in vivo suppression of cellular activity by guanidinoethyl disulfied released from hydrogel microspheres composed of partially oxidized hyaluronan and gelatin," Biomaterials, Aug. 3, 2008, vol. 29, pp. 4149-4156.
Weng, L. et al., "Self-crosslinkable hydrogels composed of partially oxidized hyaluronan and gelatin: in vitro and in vivo responses," Journal of Biomedical Materials Research Part A, Aug. 9, 2007, pp. 352-365.
Wermuth, C.G., "Similarity in drugs: reflections on analogue design," Drug Discovery Today (2006) 11(7/8):348-354.
Won, K. et al., "Horseradish Peroxidase-Catalyzed Polymerization of Cardanol in the Presence of Redox Mediators," Biomacromolecules (2003) 5(1), 1-4.
Wondraczek, H. et al., "Synthesis of highly functionalized dextran alkyl carbonates showing nanosphere formation," Carbohydrate Polymers (2011) 83:1112-1118.
Written Opinion in International Patent Application No. PCT/CZ2009/000131, dated Apr. 9, 2010, 3 pgs.
Written Opinion in International Patent Application No. PCT/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Xu, Y.-P. et al., "Kinetics of Phenolic Polymerization Catalyzed by Peroxidase in Organic Media," Biotechnology and Bioengineering (1995) 47(1):117-119.
Yamane, Shintaro et al., "Feasibility of chitosan-based hyaluronic acid hybrid biomaterial for a novel scaffold in cartilage tissue engineering," Biomaterials (2005) 26(6);611-619.

(56) References Cited

OTHER PUBLICATIONS

Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zeng, J. et al., "Photo-Induced Solid-State Crosslinking of Electrspun Poly(vinyl alcohol) Fibers," Macromolecular Rapid Communications (2005) 26:1557-1562.
Zhong, S.P. et al., "Biodegradation of hyaluronic acid derivatives by hyalurondiase," Biomaterials (1994) 15(5):359-365.
Akkara, J.A. et al., "Synthesis and Characterization of Polymers Produced by Horseradish Peroxidase in Dioxane," Journal of Polymer Science Part A: Polymer Chemistry (1991) 29(11):1561-1574.
Aldrich, Chem Files Synthetic Methods Oxidation (including English translation), May 2005, vol. 5, No. 1 pp. 1-11.
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbial. (1997) 63(7):2759-2764.
Atkins, E.D.T. et al., "The Conformation of the Mucopolysaccharides," J. Biochem vol. 128, 1972, pp. 1255-1263.
Atkins, E.D.T. et al., "The Molecular Structure of Hyaluronic Acid," Biochemical Journal (1971) 125(4):92.
Author unknown, "Readily Accessible 12-I-51Oxidant for the Conversion of Primary and Secondary Alcohols to Aldehydes and Ketones," Journal of Organic Chemistry (1983) 84:4155-4156 (English language on pp. 2-3 of document).
Author unknown, Encyclopedia of Cellulose, Asakura Publishing Co., Ltd., Nov. 10, 2000, pp. 155-156 (English language translation included).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carboxyhydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials (1993) 14(15):1154-1160.
Bezakova, Z. et al., "Effect of microwave irradiation on the molecular and structural properties of hyaluronan," Carbohydrate Polymers (2008) 73(4):640-646.
Boyer, I.J., "Toxicity of dibutyltin, tributyltin and other organotin compounds to humans and to experimental animals," Toxicology (1989) 55(3), 253-298.
Buffa, R. et al., "Branched hyaluronic acid, synthesis, analysis and biological properties," Journal of Tissue Engineering and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, et al., "Transient-state and steady-state kinetics of the oxidation of aliphatic and aromatic thiols by horseradish peroxidase," FEBS Letters (1997) 411(2-3):269-274.
Chen, L. et al., "Synthesis and pH sensitivity of carboxymethyl chitosan-based polyampholyte hydrogel for protein carrier matrices," Biomaterials (2004) 25:3725-3732.
Cornwell, M.J. et al., "A One-Step Synthesis of Cyclodextrin Monoaldehydes," Tetrahedron Letters (1995) 36(46):8371-8374.
Crescenzi, V. et al., "Novel Hydrogels via Click Chemistry: Synthesis and Potential Biomedical Applications," Biomacromolecules (2007) 8:1844-1850.
Czech Official Action in Czech Patent Application No. PV 2008-705, dated Oct. 23, 2009, 2 pgs.
Czech Official Action in Czech Patent Application No. PV 2009-835, dated Aug. 2010, 2 pgs.
Czech Official Action in Czech Patent Application No. PV 2009-836, dated Aug. 6, 2010, 2 pgs.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
Darr, A. et al., "Synthesis and characterization of tyramine-based hyaluronan hydrogels," Journal of Materials Science: Materials in Medicine (2009) 20(1), 33-44.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides—an efficient approach for the determination of the degree of substitution at C-6," Carbohydrate Research (2008) 343(18)3112-3116.
Donati, A. et al., "Solution Structure of Hyaluronic Acid Oligomers by Experimental and Theoretical NMR, and Molecular Dynamics Simulation," Biopolymers (2001) 59:434-445.
Duncan, R. et al., "Nanomedicine(s) under the Microscope," Molecular Pharmaceutics (2011) 8(6):2101-2141.
Dunford, H. B. et al., "Kinetics of the oxidation of p-aminobenzoic acid catalyzed by horseradish peroxidase compounds I and II," J Biol Chem 1975, 250(8), 2920-32.
Eenschooten, C. et al., "Preparation and structural characterisation of novel and versatile amphiphilic octenyl succinic anhydride-modified hyaluronic acid derivatives," Carbohydrate Polymers (2010) 79(3):597-605.
El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
El-Dakdouki, M.H. et al., "Development of Multifunctional Hyaluronan-Coated Nanoparticles for Imaging and Drug Delivery to Cancer Cells," Biomacromolecules (2012) 13(4):1144-1151.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 61:385-392.
European First Official Action in European Patent Application No. 10812840.6-1306, dated Jul. 2, 2013, 4 pgs.
European Second Official Action in European Patent Application No. 10812840.6-1306, dated Sep. 24, 2014, 5 pgs.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.

(56) References Cited

OTHER PUBLICATIONS

Ferruti, P. et al., "Novel Poly(amido-amine)-Based Hydrogels as Scaffolds for Tissue Engineering," Macromol. Biosci. (2005) 5:613-622.
Fleige, E. et al., "Stimuli-responsive polymeric nanocarriers for the controlled transport of active compounds: Concepts and applications," Advanced Drug Delivery Reviews (2012) 64(9):866-884.
Funakoshi, T. et al., "Novel chitosan-based hyaluronan hybrid polymer fibers as a scaffold in ligament tissue engineering," Journal of Biomedical Materials Reasearch, Part A (2005) 74A(3):338-346.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, M.A. et al., "Differential substrate behaviour of phenol and aniline derivatives during oxidation by horseradish peroxidase: kinetic evidence for a two-step mechanism," Biochim. Biophys. Acta. (2004) 1699:235-243.
Gilabert, M.A. et al., "Kinetic characterization of phenol and aniline derivates as substrates of peroxidase," Biol. Chem. (2004) 385(9):795-800.
Gilabert, M.A. et al., "Stereospecificity of horseradish peroxidase," Biol. Chem. (2004) 385:1177-1184.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Gong, J. et al., "Polymeric micelles drug delivery system in oncology," Journal of Controlled Release (2012) 159(3):312-323.
Guillaumie, F. et al., "Comparative studies of various hyaluronic acids produced by microbial fermentation for potential topical ophthalmic applications," Journal of Biomedical Materials Research Part A (2009) 1421-1430.
Gupta, P. et al., "Hydrogels: from controlled release to pH-responsive drug delivery," Drug Discovery Today (2002) 7(10):569-579.
Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hewson, W. D. et al., "Oxidation of p-cresol by horseradish peroxidase compound I," J Biol Chem 1976, 251 (19), 6036-42.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hoffman, A.S. "'Intelligent' Polymers in Medicine and Biotechnology," Artificial Organs (1995) 19(5):458-467.
Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62(3):611-620.
Huang, G. et al., "Superparamagnetic Iron Oxide Nanoparticles: Amplifying ROS Stress to Improve Anticancer Drug Efficacy.," Theranostics (2013) 3(2):116-126.
Huerta-Angeles, G. et al., "Synthesis of highly substituted amide hyaluronan derivatives with tailored degree of substitution and their crosslinking via click chemistry," Carbohydrate Polymers (2011) 84:1293-1300.
Huh, K.M. et al., "Hydrotropic polymer micelle system for delivery of paclitaxel," Journal of Controlled Release (2005) 101:59-68.
Hynes, W.L. et al., "Hyaluronidases of Gram-positive bacteria," FEMS Microbiology Letters (2000) 183:201-207.
Inanaga, J. et al., "A Rapid Esterification by Means of Mixed Anhydride and Its Application to Large-ring Lactonization," Bulletin of the Chemical Society of Japan (1979) 52(7):1989-1993.
International Search Report in International Patent Application No. PCT/CZ2009/000131, dated Apr. 9, 2010, 3 pgs.
International Search Report in International Patent Application No. PCT/CZ2010/000030, dated Sep. 1, 2010, 3 pgs.
International Search Report in International Patent Application No. PCT/CZ2010/000128, dated Jun. 9, 2011, 3 pgs.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pgs.
International Search Report in International Patent Application No. PCT/CZ2012/000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000057, dated Jul. 24, 2013, 4 pgs.
International Search Report in International Patent Application No. PCT/CZ2013/000063, dated Apr. 23, 2015, 7 pgs.
International Search Report in International Patent Application No. PCT/CZ2013/000091, dated Oct. 31, 2013, 3 pgs.
International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pgs.
Jia. X.Q., et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB (2000) 327(4)455-461.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Office Action in U.S. Appl. No. 14/647,626, dated Jun. 16, 2017, 14 pgs.
Office Action in U.S. Appl. No. 14/647,649, dated May 31, 2017, 11 pgs.
Office Action in U.S. Appl. No. 14/430,731, dated May 19, 2016, 12 pgs.
Office Action in U.S. Appl. No. 14/647,185, dated Sep. 28, 2016, 5 pgs.
Office Action in U.S. Appl. No. 14/647,626, dated Feb. 17, 2017, 12 pgs.
Office Action in U.S. Appl. No. 14/647,626, dated Jul. 28, 2016, 35 pgs.

(56) References Cited

OTHER PUBLICATIONS

Oh, E.J. et al., "Target specific and long-acting delivery of protein, peptide, and nucleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., "Photopolymerized hyaluronic acid-based hydrogels and interpenetrating networks," Biomaterials (2003) 24:893-900.
Patel, P.K. et al., "Kinetic studies on the oxidation of phenols by the horseradish peroxidase compound II," Biochim Biophys Acta (1997) 1339(1):79-87.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II, Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Ruoslahti, E. et al., "Targeting of drugs and nanoparticles to tumors," The Journal of Cell Biology (2010) 188(6):759-768.
Rupprecht, A., "Wet Spinning of Hyaluronic Acid. Preparation of Oriented Samples," Acta. Chem. Scant vol. B33, No. 10, 1979, pp. 779-780.
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., "X-ray Diffraction Studies on the Connective Tissue Polysaccharides," J. Mol. Biol. (1975) 91:153-163.
Shen, Y. et al., "Synthesis and characterization of low molecular weight hyaluronic acid-based cationic micelles for efficient siRNA delivery," Carbohydrate Polymers (2009) 77(1):95-104.
Shen, Yi et al., "Synthesis, Characterization, Antibacterial and Antifungal Evaluation of Novel Monosaccharide Esters," Molecules (2012) 17(7):8661-8673.
Shimizu, M. et al., "Studies on hyaluronidase, chondroitin sulphatase, proteinase and phospholipase secreted by *Candida* species," MYCOSES (1996) 39:161-167.
Shutava, T. et al., "Microcapsule Modification with Peroxidase-Catalyzed Phenol Polymerization," Biomacromolecules (2004) 5(3):914-921.
Sieburth, S.M. et al., "Fusicoccin Ring System by [4+4} Cycloaddition. 2. A Model Study," Tetrahedron Letters (1999) 40:4007-4010.
Sieburth, S.M. et al., "The [4+4] Cycloaddition and its Strategic Application in Natural Product Synthesis," Tetrahedron (1996) 52(18):6251-6282.
Slaughter, B.V. et al., "Hydrogels in Regenerative Medicine," Advanced Materials (2009) 21(32-33):3307-3329.
Slezingrova, K. et al., "Synteza a charakterizace palmitoyl hyaluronanu," Chemicke Listy (2012) 106:554-567.
Smeds, K.A. et al., "Photocrosslinkable polysaccharides for in situ hydrogel formation," J. Biomed. Mater. Res. (2001) 54:115-121.
Smejkalova, D. et al., "Structural and conformational differences of acylated hyaluronan modified in protic and aprotic solvent system," Carbohydrate Polymers (2012) 87(2):1460-1466.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H. et al., "Injectable in situ forming biodegradable chitosan-hyaluronic acid based hydrogels for cartilage tissue engineering," Biomaterials (2009) 30(13):2499-2506.
Tankam, P.F. et al., "Alkynyl polysaccharides: synthesis of propargyl potato starch followed by subsequent derivatizations," Carbohydrate Research (2007) 342:2049-2060.
Tao, Y. et al., "Core cross-linked hyaluronan-styrylpyridinium micelles as a novel carrier for paclitaxel," Carbohydrate Polymers (2012) 88(1):118-124.
Testa, G. et al., "Influence of dialkyne structure on the properties of new click-gels based on hyaluronic acid," International Journal of Pharmaceutics (2009) 378:86-92.
Thakar, D. et al., "A quartz crystal microbalance method to study the terminal functionalization of glycosaminoglycans," Chemical Communications (2014) 50(96):15148-15151.
Til, H.P. et al., "Acute and Subacute Toxicity of Tyramine, Spennidine, Spennine, Putrescine and Cadaverine in Rats," Food and Chemical Toxicology (1997) 35(3-4):337-348.
Tonelli, A.E., "Effects of crosslink density and length on the number of intramolecular crosslinks (defects) introduced into a rubbery network," Polymer (1974) 15(4):194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.
International Search Report in International Patent Application No. PCT/CZ2016/000027, dated Jun. 27, 2016, 3 pgs.
Written Opinion in International Patent Application No. PCT/CZ2016/000027, dated Jun. 27, 2016, 6 pgs.
Breunig, M. et al., "Breaking up the correlation between efficacy and toxicity for nonviral gene delivery," PNAS (2007) 104(36):14454-14459.

(56) References Cited

OTHER PUBLICATIONS

Thomas et al, "Hyaluronic acid conjugated superparamagnetic iron oxide nanoparticle for cancer diagnosis and hyperthermia therapy," Carbohydrate Polymers 131 (2015) pp. 439-446.
Yang, Rui-Meng et al., "Hylauronan-modified superparamagnetic iron oxide nanoparticles for bimodal breast cancer imaging and photothermal therapy," Int'l J. of Nanomedicine 2017: 12, pp. 197-206.
Zeng, Yuan-Xian et al., "Preparation and Enhancement of Thermal Conductivity of Heat Transfer Oil-Based MoS2 Nanofluids," Journal of Nanomaterials, vol. 2013, Art. ID 270490, 6 pgs.
Office Action in U.S. Appl. No. 15/124,827, dated Dec. 7, 2017, 9 pgs.
Office Action in U.S. Appl. No. 15/556,370, dated Aug. 2, 2018, 18 pgs.
Office Action in U.S. Appl. No. 15/737,894, dated Oct. 5, 2018, 27 pgs.
Pasqui, D. et al., "Polysaccharide-Based Hydrogels: The Key Role of Water in Affecting Mechanical Properties," Polymers (2012) 4:1517-1534.
Perale, G. et al., "Hydrogels in Spinal Cord Injury Repair Strategies," ACS Chem. Neurosci. (2011) 2(7):336-345.
Piggot, A.M. et al., "Synthesis of a new hydrophilic o-nitrobenzyl photocleavable linker suitable for use in chemical proteomics," Tetr. Lett. (2005) 46(47):8241-8244.
Price, Richard D. et al., "Hyaluronic acid: the scientific and clinical evidence," J. Plast. Reconstr. Aesthet. Surg. (2007) 60(10):1110-1119.
Rowe et al., "Handbook of Pharmaceutical Excipients," 6th edition, 2009, Pharmaceutical Press, pp. 110-114 and 581-585. (Year: 2009).
Saettone et al., "Evaluation of muco-adhesive properties and in vivo activity of ophthalmic vehicles based on hyaluronic acid," 1989, International Journal of Pharmaceutics, vol. 51, pp. 203-212. (Year: 1989).
Su, W.Y. et al., "Injectable oxidized hyaluronic acid/adipic acid dihydrazide hydrogel for nucleus pulposus regeneration," Acta. Biomater. (2010) 6(8):3044-3055.
Tan, X. et al., "A NIR heptamethine dye with intrinsic cancer targeting, imaging and photosensitizing propeties," Biomaterials (2012) 33:2230-2239.
Thelin, M. et al., "Biological functions of iduronic acid in chondroitin/dermatan sulfate," FEBS Journal (2013) 280:2431-2446.
Wang, W. et al., "Developing Fluorescent Hyaluronan Analogs for Hyaluronan Studies," Molecules 2012, 17, 1520-1534.
Weng L., et al., "Self-crosslinkable hydrogels composed of partially oxidized hyaluronan and gelatin: In vitro and in vivo responses," Journal of Biomedical Materials Research Part A, 85:352-365.
Werner, T. et al., "Simple Method for the Preparation of Esters from Grignard Reagents and Alkyl 1-Imidazolecarboxylates," J. Org. Chem. (2006) 71(11):4302-4304.
Written Opinion in International Patent Application No. PCT/CZ2016/000065, dated Sep. 30, 2016, 5 pgs.
Written Opinion in International Patent Application No. PCT/CZ2016/000071, dated Oct. 10, 2016, 5 pgs.
Written Opinion in International Patent Application No. PCT/CZ2016/050036, dated Feb. 6, 2017, 6 pgs.
Written Opinion in International Patent Application No. PCT/CZ2016/050048, dated May 3, 2017, 6 pgs.
Written Opinion in International Patent Application No. PCT/EP2016/064653, dated Aug. 25, 2016, 6 pgs.
Xu, Y. et al., "Feasibility study of a novel crosslinking reagent (alginate dialdehyde) for biological tissue fixation," Carbohydrate Polymers (2012) 87(2):1589-1595.
Ye, Y. et al., "Multivalent Carbocyanine Molecular Probes: Synthesis and Applications," Bioconjugate Chem. 2005, 16, 51-61.
Ye, Y. et al., "Novel Near-Infrared Fluorescent Integrin-Targeted DFO Analogue," Bioconjugate Chem. (2008) 19:225-234.
Ye, Y. et al., "Polyvalent Carbocyanine Molecular Beacons for Molecular Recognitions," J. Am. Chem. Soc. 2004, 126, 7740-7741.
Ye, Y.; et al., "Integrin Targeting for Tumor Optical Imaging," Theranostics 2011, 1, 102-126.
Zaafarany, I. et al., "Oxidation of Some Sulfated Carbohydrates: Kinetics and Mechanism of Oxidation of Chondroitin-4-Sulfate by Alkaline Permanganate with Novel Synthesis of Coordination Biopolymer Precursor," J. Mat. Sci. Res. (2013) 2(4):23-36.
Zou, X.H. et al., "Specific interactions between human fibroblasts and particular chondroitin sulfate molecules for wound healing," Acta Biomaterialia (2009) 5(5):1588-1595.
Aubry-Rozier, B., Revue Medicale Suisse (2012) 14:571.
Baeurle, S.A. et al., "Effect of the counterion behavior on the frictional-compressive properties of chondroitin sulfate solutions," Polymer (2009) 50(7):1805-1813.
Baijal, K. P. et al., "Tumor-enhancing effects of cholic acid are exerted on the early stages of colon carcinogenesis via induction of aberrant crypt foci with an enhanced growth phenotype," Canadian Journal of Physiology and Pharmacology, 1998, 76(12), 1095-1102.
Balan, V. et al., "Strategies to improve chitosan hemocompatibility: A review," European Polymer Journal (2004) 53:171-188.
Bottegoni, C. et al., "Oral chondroprotection with nutraceuticals made of chondroitin sulphate plus glucosamine sulphate in osteoarthritis," Carb. Pol. (2014) 109:126-138.
Carey, F.A. et al., Advanced Organic Chemistry Part A: Structure and Mechanisms, Plenum Press, New York and London, pp. 475-479 (1990).
Chen, H. et al., "A dual-targeting nanocarrier based on modified chitosan micelles for tumor imaging and therapy," Polym. Chem. 2014, 5, 4734-4746.
Cherrick, G. R. et al., "Indocyanine Green: Observations on Its Physical Properties, Plasma Decay, and Hepatic Extraction," J.Clinical Investigation, 1960, 39, 592-600.
Choi, K. Y. et al., "Self-assembled hyaluronic acid nanoparticles as a potential drug carrier for cancer therapy: synthesis, characterization, and in vivo biodistribution," J. Mater. Chem. 2009, 19 (24), 4102-4107.
Choi, K. Y. et al., "Self-assembled hyaluronic acid nanoparticles for active tumor targeting," Biomaterials 2010, 31 (1), 106-114.
Choi, W. II et al., Targeted antitumor efficacy and imaging via multifunctional nano-carrier conjugated with anti-HER2 trastuzumab, Nanomedicine: Nanotechnology, Biology, and Medicine (2015) 11:359-368.
Chu et al., "Electro-Spinning and Electro-Blowing of Hyaluronic Acid," 2004, Biomacromolecules, vol. 5, pp. 1428-1436. (Year: 2004).
Contipro, Specialty Hyaluronan Chemicals Product Catalog, 52 pgs. (retrieved on Sep. 26, 2018). (Year: 2018).
Cumpstey, I., Review Article "Chemical Modification of Polysaccharides," ISRN Organic Chemistry (2013) Article ID 417672, 27 pgs.
D'Este, M. et al., "A systematic analysis of DMTMM vs EDC/NHS for ligation of amines to Hyaluronan in water," Carbohydr. Polym. 2014, 108, 239-246.
Dawlee, S. et al., "Oxidized Chondroitin Sulfate-Cross-Linked Gelatin Matrixes: A New Class of Hydrogels," Biomacromolecules (2005) 6(4):2040-2048.
De Figueiredo, R.M. et al., "N,N'-Carbonyldiimidazole-Mediated Cyclization of Amino Alcohols to Substituted Azetidines and Other N-Heterocycles," J. Org. Chem. (2006) 71(11):4147-4154.
Frangioni, J. V., "In vivo near-infrared fluorescence imaging," Curr. Opin. Chem. Biol. (2003) 7(5):626-634.
Funfstuck, V. V. et al., "Kontaktallergie gegenuber Dicyclohexylcarbodiimid," Dermatosen (1986) 34(4):110-111.
Furuta, T. et al., "Anthraquinon-2-ylmethoxycarbonyl (Aqmoc): A New Photochemically Removable Protecting Group for Alcohols," Org. Lett. (2001) 3(12):1809-1812.
Gobouri, A.A. et al., "Novel Synthesis of Diketo-Acid Chondroitin-4-sulfate as Coordination Biopolymer Precursor through Oxidation of Chondroitin-4-sulfate by Alkaline Permanganate," International Journal of Sciences (2013) 7:1-11.
Green, T.W. et al., "Protective Groups in Organic Synthesis," 1999, New York: John Wiley & Sons, 3rd ed., Chap. 1, pp. 1-16.

(56) References Cited

OTHER PUBLICATIONS

Hassan, R. et al., "Kinetics and mechanism of oxidation of chondroitin-4-sulfate polysaccharide by chromic acid in aqueous perchlorate solutions," (2013) Carbohydrate Polymers 92:2321-6.
Hill, T. K. et al., "Indocyanine Green-Loaded Nanoparticles for Image-Guided Tumor Surgery," Bioconjugate Chem. (2015) 26:294-303.
Huang, L. et al., "A Facsimile Method for Oxidation of Primary Alcohols to Caroxylic Acids and Its Application in Glycosaminoglycan Syntheses," Chemistry (2006) 12(20):5246-5252.
Huerta-Angeles, G. et al., "Novel synthetic method for the preparation of amphiphilic hyaluronan by means of aliphatic aromatic anhydrides," Carbohydrate Polymers (2014) 111:883-891.
Hussain, M. A. et al., "Acylation of Cellulose with N,N'-Carbonyldiimidazole-Activated Acids in the Novel Solvent Dimethyl Sulfoxide/Tetrabutylammonium Fluoride," Macromol. Rapid Commun. (2004) 25:916-920.
International Search Report in International Patent Application No. PCT/CZ2016/000065, dated Sep. 30, 2016, 5 pgs.
International Search Report in International Patent Application No. PCT/CZ2016/000071, dated Oct. 10, 2016, 4 pgs.
International Search Report in International Patent Application No. PCT/CZ2016/050036, dated Feb. 6, 2017, 4 pgs.
International Search Report in International Patent Application No. PCT/CZ2016/050048, dated May 3, 2017, 4 pgs.
International Search Report in International Patent Application No. PCT/EP2016/064653, dated Aug. 25, 2016, 4 pgs.
Japanese Official Action in Japanese Patent Application No. 2015-543316, 5 pgs.
Ji, Y. et al., "Electrospun three-dimensional hyaluronic acid nanofibrous scaffolds," Biomaterials (2006) 27(1):3782-3792.
Katz, S.A. et al., "The Toxicology of Chromium with Respect to its Chemical Speciation: a Review," Journal of Applied Toxicology (1993) 13(3):217-224.
Khetan, S. et al., "Patterning network structure to spatially control cellular remodeling and stem cell fate within 3-dimensional hydrogels," Biomaterials (2010) 31(32):8228-8234.
Klan, P. et al., "Photoremovable Protecting Groups in Chemistry and Biology: Reaction Mechanisms and Efficacy," Chem. Rev. (2013) 113(1):119-191.
Kobayashi, H. et al., "New Strategies for Fluorescent Probe Design in Medical Diagnostic Imaging," Chem. Rev. (2010) 110(5):2620-2640.
Kokuryo, D. et al., "Corrigendum to SPIO-PICsome: Development of a highly sensitive and stealth-capable MRI nano-agent for tumor detection using SPIO-loaded unimellar polyion complex vesicles (PICsomes)," Journal of Controlled Release (2014) 178:125.
Lee, Dong-Eun et al., "Hyaluronidase-Sensitive SPIONs for MR/Optical Dual Imaging Nanoprobes," Marcomol. Res. (2011) 19(8):861-867.
Liang, Y. et al., "An in situ formed biodegradable hydrogel for reconstruction of the corneal endothelium," Colloids and Surfaces B: Biointerfaces (2011) 82(1):1-7.
Luo, S. et al., "A review of NIR dyes in cancer targeting and imaging," Biomaterials (2011) 32:7127-7138.
Miki, K. et al., "Near-Infrard Dye-Conjugated Amphiphilic Hyaluronic Acid Derivatives as a Dual Contrast Agent for In Vivo Optical and Photoacoustic Tumor Imaging," Biomacromolecules (2015) 16:219-227.
Normandin, L. et al., "Manganese Neurotoxicity: An Update of Pathophysiologic Mechanisms," Metab Brain Dis (2002) 17(4):375-387.
Office Action in U.S. Appl. No. 14/647,626, dated Nov. 13, 2017, 18 pgs.
Office Action in U.S. Appl. No. 14/647,649, dated Apr. 19, 2018, 9 pgs.
Office Action in U.S. Appl. No. 14/647,649, dated Dec. 8, 2017, 9 pgs.
Office Action in U.S. Appl. No. 15/038,078, dated Mar. 1, 2018, 10 pgs.
Office Action in U.S. Appl. No. 15/038,078, dated Nov. 3, 2017, 10 pgs.
Office Action in U.S. Appl. No. 15/038,078, dated Sep. 11, 2018, 9 pgs.
Bobula, T. et al., "One-pot synthesis of alpha,beta-unsaturated polyaldehyde of chondroitin sulfate," Carbohydrate Polymers (2016) 136:1002-1009.
Bobula, T. et al., "Solid-state photocrosslinking of hyaluronan microfibres," Carbohydrate Polymers (2015) 125:153-160.
Brand-Williams, W. et al., "Use of a Free Radical Method to Evaluate Antioxidant Activity," LWT-Food Science and Technology (1995) 28:25-30.
Collins, M. N. et al., "Hyaluronic Acid Based Scaffolds for Tissue Engineering—A review," Carbohydrate Polymers (2013) 92:1262-1279.
Hacker, M. C. et al., "Multi-Functional Macromers for Hydrogel Design in Biomedical Engineering and Regenerative Medicine," Inter. J. of Mol. Sc. (2015) 16:27677-27706.
Horton, D. et al., "Synthethis of 2,3-Unsaturated Polysaccharides From Amylose and Xylan," Carbohydrate Research (1975) 40:345-352.
International Search Report in International Patent Application No. PCT/CZ2017/050026, dated Oct. 26, 2017, 2 pgs.
Kelly, S. J. et al., "Kinetic properties of Streptococcus pneumoniae hyaluronate lyase," Glycobiology (2001) 11(4):297-304.
Khetan, S. et al., "Sequential crosslinking to control cellular spreading in 3-dimensional hydrogels," Soft Matter (2009) 5:1601-1606.
Kühn, A. V. et al., "Identification of hyaluronic acid oligosaccharides by direct coupling of capillary electrophoresis with electrospray ion trap mass spectrometry," Rapid Communications in Mass Spectrometry (2003) 17:576-582.
Mero, A. et al., "Hyaluronic Acid Bioconjugates for the Delivery of Bioactive Molecules," Polymers (2014) 6(2):346-369.
Nimmo, C. M. et al., "Diels-Alder Click Cross-Linked Hyaluronic Acid Hydrogels for Tissue Engineering," Biomacromolecules (2011) 12:824-830.
Vigo, T. L. et al., "Deoxycelluloses and Related Structures," Polymers for Advanced Technologies (1999) 10:311-320.
Written Opinion in International Patent Application No. PCT/CZ2017/050026, dated Oct. 26, 2017, 5 pgs.
Foglarova, Marcela et al., "Water-insoluble thin filmis from palmitoyl hyaluronan with tunable properties," Carbohydrate Polymers (2016) 144:68-75.
Khademhosseini, A. et al., "Layer-by-layer deposition of hyaluronic acid and poly-L-lysine for patterned cell co-cultures," Biomaterials (2004) 25:3583-3592.
Mondek, J. et al., "Thermal degradation of high molar mass hyaluronan in solution and in powder; comparison with BSA," Polymer Degradation and Stability (2015) 120:107-113.
Office Action in U.S. Appl. No. 14/647,649, dated Dec. 13, 2018, 9 pgs.
Office Action in U.S. Appl. No. 15/038,078, dated Dec. 21, 2018, 9 pgs.
Office Action in U.S. Appl. No. 15/556,370, dated May 10, 2019, 17 pgs.
Office Action in U.S. Appl. No. 15/556,370, dated Sep. 17, 2019, 20 pgs.
Office Action in U.S. Appl. No. 15/737,443 dated Feb. 20, 2019, 13 pgs.
Office Action in U.S. Appl. No. 15/737,894, dated Jun. 25, 2019, 32 pgs.
Schachter, D., "The Source of Toxicity in CTAB and CTAB-Stabilized Gold Nanorods," MS thesis submitted to Graduate School-New Brunswick Rutgers, The State University of New Jersey and The Graduate School of Biomedical Sciences, University of Medicine and Dentistry of New Jersey, 2013, 70 pgs.
Young, Denice S., "Hyaluronic Acid-based Nanofibers via Electrospinning," M.S. Thesis of Denice S. Young, North Carolina State University (2006) pp. 1-97.

* cited by examiner

ANTITUMOR COMPOSITION BASED ON HYALURONIC ACID AND INORGANIC NANOPARTICLES, METHOD OF PREPARATION THEREOF AND USE THEREOF

FIELD OF THE ART

The invention relates to a composition based on hyaluronic acid which may be used for treatment of tumorous diseases. The composition includes polymeric nanomicelles comprising a hydrophobized derivative of hyaluronic acid or a pharmaceutically acceptable salt thereof, and nanoparticles stabilized by means of oleic acid, preferably superparamagnetic nanoparticles of iron, nanoparticles of zinc or up-conversion nanoparticles.

PRIOR ART

In treatment of tumorous diseases, chemotherapy is most frequently used, where the patient is intravenously or orally administered medicinal substances which are system-distributed into the whole body. However, the antitumor substances are highly toxic not only in respect to the tumor cells but also in respect to the healthy cells. The consequence of the systemic distribution then is the toxicity of antitumor therapeutics not only in the areas with a tumorous disease, but also in the areas of healthy tissues and cells. Moreover, the non-selective distribution of the drug decreases the amount of the medicinal substance which reaches the tumor cells in the end, thereby reducing the effectivity of the therapy.

Due to the above mentioned facts, there exists an enormous interest in finding a suitable strategy which would allow enhancing the chemotherapeutic effectivity towards the tumor cells and at the same time suppressing the undesirable systemic toxicity of the therapeutics. It was found out that the undesirable side-effects of medicinal substances are suppressed in a great extent, sometimes even eliminated, if the drug is incorporated in a matrix of carrier systems. For this purpose, the research is often aimed at targeting of such carrier systems to the tumor cells.

Nowadays, there are two most frequent strategies used for targeting. One of them is based on the so-called passive targeting where an increased permeability and retention of tumorous tissues is used (the so-called EPR effect) (Maeda, 2001), As opposed to the healthy tissues, the tumor tissues are characterized by a perforated vascularity by means of which nanometer-sized molecules may get from the bloodstream to the tumor. The passive targeting is, however, besides other factors, limited by a little-effective and non-specific catching of carrier systems with a medicinal substance by the tumor cells (Duncan & Gaspar, 2011; El-Dakdouki, Pure & Huang, 2013). If, however, the carrier system has a suitable size for passive targeting, such method of targeting may be associated with an enhanced anti-tumor effect of the given therapeutic with respect to the tumor cells due to other properties of the carrier. For example the patent application No. WO2008/130121 claims a tumor-selective and biodegradable cyclotriphosphazene-platinum (II) conjugate which forms polymeric micelles in aqueous solutions and, compared to the similar conjugates of US2001/6333422, exhibits an enhanced selectivity in passive targeting to tumor tissues. The enhanced selectivity with respect to the tumor cells in passive targeting is also mentioned in the patent application No. WO2013/188727 which discloses biodegradable PEGylated nanoparticles comprising a conjugate of the medicinal substance (SN-38, PI-103, etopo side, phenretinide) with a retinoate or an isomer thereof, bound by means of a rapidly cleaving esteric phenolic bond. The enhanced selectivity was, in both cases, detected based on experimental data when compared to similar systems.

Another method to make the targeting and thereby the selectivity of the drug action more effective is the possibility when the therapeutics are modified by ligands having a high affinity to the receptors located on the surface of the tumor cells (Duncan & Gaspar, 2011; Ruoslahti, Bhatia & Sailor, 2010). This second strategy, which is known as active targeting, should ensure a selective distribution of the therapeutic into the tumor cells. An example may be e.g. the solution disclosed in US2007/0155807 where derivatives of carboxylic acids of thiazolidinone amides and thiazolidinine amides are claimed, in which selective behaviour towards melanoma cells exhibiting an increased LPL receptor expression was detected. The disadvantage of this and similar solutions is the fact that LPL receptors are expressed in healthy cells as well, e.g. cardiomyocytes, which may lead to their selective action in a healthy tissue, too. Another disadvantage of this and other similar solutions (e.g. WO 2012/173677, US 2013/02742200) is the fact that the expression of the tumor cell receptors is variable not only in time but also in patients (Duncan & Gaspar, 2011). The selected bound ligand for active targeting then may have an effect just on cells in a certain stage of the tumor disease or just on some of the patients.

Another possibility of active targeting lies in targeting of the carrier systems by means of an external magnetic field in the cases where the systems comprise either covalently or non-covalently bound magnetic nanoparticles. In said case, superparamagnetic nanoparticles (SPIONs) may be preferably used. Most frequently, these are $Fe_3O_4$ nanoparticles which are regarded as inert contrast MRI means without any intended pharmacological function (Huang et al., 2013). No short-term or long-term toxicity has been reported so far for SPIONs after the internalisation thereof in a cell (Huang et al., 2013). Besides MRI contrast and magnetic targeting, SPIONs may be used as carriers in combination with cytostatics or other medicinal substances. Another preferred use is the magnetic fluid hyperthermia in which the SPIONs absorb the alternating magnetic field energy and transform it into heat. Therefore, it is possible to selectively increase the temperature in the area where the SPIONs are located. If the SPIONs are located in the area of the tumor, it is possible to destroy the tumor cells by means of an elevated temperature, because they are more temperature-sensitive than the healthy cells (Laurent, Dutz, Hafeli & Mahmoudi, 2011).

In combination with passive or active targeting, several distinguishing properties of the tumor cells, as compared to the healthy cells, are used in order to enhance the selectivity of the therapeutic (Fleige, Quadir & Haag, 2012). These properties include e.g. a more acid pH or an elevated level of the reactive forms of oxygen (ROS). The patent application No. US2013/0230542 discloses therapeutic components (phenol derivatives) which are activated in the environment where ROS are present, and, therefore, they should act selectively in tumor cells having an elevated level of ROS. A disadvantage of said solution is the fact that the elevated ROS level is in certain healthy cells as well. Examples are macrophages where the high level of ROS allows for elimination of pathogens in phagozomes. An elevated ROS level serves also in other cells as a natural defence mechanism against hypoxia and also as signal molecules affecting a number of physiological functions.

In literature, there are also antitumor compositions which are promising in that in vitro, they act in an antitumor manner with respect to some types of tumor cells. An example is the composition of US 2005/0255173 comprising one to three components selected from the following group: citric acid, zinc and albumin. Said composition was more cytotoxic in vitro against human cell lines derived from adenocarcinomas NIH:OV-CAR-3 and SKOV-3 compared to control cells WI38 (normal human lung fibroblasts). A drawback of said composition is the fact that its antitumor effect depends on the concentration content of the individual components (US 2005/0255173). Since the components are body-innate, the effect of the claimed composition may be influenced by the local concentration of individual substances in the given place of administration (e.g. a high concentration of albumin in blood).

The cited literature shows that the research of antitumor therapeutics runs worldwide. However, the success of clinical use of the proposed solutions is still a challenge, especially due to the fact that most of the solutions include organic polymers which are not biodegradable and that they do not have a sufficient selectivity towards tumor cells. On that account, there still exists an interest in finding new compositions having selective effects on tumor cells.

SUBJECT-MATTER OF THE INVENTION

The subject-matter of the invention lies in hyaluronan nanomicelles combined with inorganic nanoparticles as selective antitumor therapeutics. More specifically, the invention relates to a composition based on hydrophobized hyaluronic acid and inorganic nanoparticles, which acts selectively with respect to the cells derived from colorectum carcinoma or adenocarcinoma, lung carcinoma, hepatocellular carcinoma and breast carcinoma. The composition may also be used as an in vivo contrast medium. Further, the invention relates to the method of preparation of said composition.

The composition is based on loading of inorganic nanoparticles, stabilized by oleic acid, into nanomicelles of hydrophobized hyaluronan. Loading may be performed by sonication of solutions of nanoparticles in an organic solvent with a solution of hydrophobized hyaluronan in water. The resulting nanomicelles comprising inorganic nanoparticles are then subjected to centrifugation and separated thereby from the free inorganic nanoparticles and may be used for selective effect on tumor cells. The main and unique advantage of the composition of the invention is its selective activity in vitro with respect to tumor cells, even in case when a mixture of tumor and control cells is treated. The composition contains inorganic nanoparticles, stabilized by oleic acid, wherein the original purpose of inorganic nanoparticles was to allow an in vivo detection of the composition after its administration into the body. However, it was surprisingly found out that in combination with the hydrophobized hyaluronic acid, especially hyaluronic acid oleyl derivative, the said composition is selectively cytotoxic with respect to the tumor cells in vitro even without any cytostatic or other therapeutic substance. This unexpected, and unexplained so far, effect was observed for SPION nanoparticles, zinc oxide nanoparticles and upconversion nanoparticles, provided that they are stabilized by oleic acid. The unexpected effect can neither be distinctly explained as a receptor-mediated effect, mediated via CD44 receptors which are specific for hyaluronan, nor, can the observed selectivity be, according to the data collected up till now, associated with the influence of an increased ROS production. However, the selectivity may be caused by another mechanism of an intracellular release of nanoparticle ions. The selective effect on tumor cells is all the more surprising that the SPIONs incorporated in the carriers based on a polysaccharide or another polymer matrix are used to be interpreted as non-cytotoxic (El-Dakdouki et al., 2012; Li, Kim, Tian, Yu, Jon & Moon, 2012).

Other advantages of said composition include the compatibility with physiological solutions, the possibility of an intravenous administration in vivo and the stability of nanomicelles in time at physiological pH. Another advantage of the composition is the use of hyaluronan as the carrier polymer which forms an envelope around nanomicelle systems, whereby ensuring the compatibility of the composition for an in vivo administration. Preferably, hyaluronan may also support the bonding of said composition to the tumor cells, characterized by an increased expression of CD44 receptor. The presence of SPIONs in the composition may preferably be used for targeting of carriers into the desired location in the body by means of the magnetic field. An alternating magnetic field may serve for inducing hyperthermia leading to the destruction of the tumor tissue. Another advantage is that the given composition may be combined with other active substances, such as cytostatics. Similarly to the SPIONs and zinc oxide nanoparticles, the presence of upconversion nanoparticles may be preferably used for an in vivo detection of the composition in the tissue. Moreover, the upconversion nanoparticles having a specific composition may be used for photodynamic therapy or for controlled-release of a medicament from the composition. The presence of zinc oxide nanoparticles may be preferably used in tumor tissues having a more acid pH, where the ZnO nanoparticles may dissolve and $Zn^{2+}$ ions are released, while being locally cytotoxic in higher concentrations.

Therefore, the invention relates to an anti-tumor composition based on acylated hyaluronan and inorganic nanoparticles stabilized by oleic acid and selected from the group comprising superparamagnetic nanoparticles, upconversion nanoparticles or zinc oxide nanoparticles, especially superparamagnetic nanoparticles. The acylated hyaluronan may be a $C_6$-$C_{18}$-acylated derivative of hyaluronic acid having saturated and unsaturated bonds, especially the $C_{18:1}$ acylated derivative of hyaluronic acid, and said acylated hyaluronan serves as a carrier of inorganic nanoparticles. In case the composition according to the invention contains superparamagnetic nanoparticles, these are preferably nanoparticles based on oxides of iron where the amount of Fe in the composition is 0.3 to 3% by weight, preferably 1.0% by weight. The size of the superparamagnetic nanoparticles is 5 to 20 nm, preferably 5-7 nm, more preferably 5 nm. In case the anti-tumor composition contains zinc oxide nanoparticles, these are present therein preferably in an amount of 0.3 to 3% by weight of Zn. In case the anti-tumor composition contains upconversion nanoparticles, these are preferably present in such an amount that the total amount of the rare-earth elements in the composition is 0.3 to 3% hm. The upconversion nanoparticles may comprise e.g. Er, Yb and Y. The advantage of the composition according to the invention composition is also the fact that it is possible to be sterilized in the final package by means of autoclaving.

The anti-tumor composition according to the invention may be used especially for an inhibition of the growth of both adherent and suspension human tumor cell lines derived from colorectum carcinoma and adenocarcinoma, lung carcinoma, hepatocellular carcinoma, breast carcinoma, preferably colorectum carcinoma and adenocarcinoma. Further, the anti-tumor composition comprising superparamagnetic nanoparticles may be used as an in vivo contrast substance, i.e. for detection of accumulation of the composition in the body, especially in liver and pathologic formations, e.g. in tumors. It was found out that the composition according to the invention exhibits a different manner of releasing metal ions, in vitro in tumor and non-tumor cells, especially in cells derived from human colorectum adenocarcinoma (=tumor) and human dermal fibroblasts (=non-tumor).

The anti-tumor composition according to the invention may be applied in a formulation for parenteral or local administration, e.g. intravenously. It may further comprise other additives used in pharmaceutical compositions, preferably sodium chloride, dextrose or buffering salts.

The composition according to the invention can be prepared in the following way: an aqueous solution of acylated derivative of hyaluronic acid is prepared, then inorganic particles dispersed in a halide solvent, e.g. chloroform, are added, the inorganic particles being stabilized by oleic acid and selected from the group comprising superparamagnetic nanoparticles, upconversion nanoparticles or zinc oxide nanoparticles, and the resulting suspension is sonicated until a homogenous mixture is formed, and then the free inorganic nanoparticles are separated from the inorganic nanoparticles loaded in nanomicelles by means of centrifugation and a subsequent filtration. The filtrate may then be lyophilized or sterilized by autoclaving for the purpose of a long-term storage. The lyophilizate may then be dissolved in an aqueous solution and sterilized by autoclaving.

For the purpose of the invention, commercially available SPIONs may be used, stabilized by oleic acid.

LITERATURE

Duncan, R., & Gaspar, R. (2011). Nanomedicine(s) under the Microscope. *Molecular Pharmaceutics,* 8(6), 2101-2141.

El-Dakdouki, M. H., Pure, E., & Huang, X. (2013). Development of drug loaded nanoparticles for tumor targeting. Part 1: synthesis, characterization, and biological evaluation in 2D cell cultures. *Nanoscale,* 5(9), 3895-3903.

El-Dakdouki, M. H., Zhu, D. C., El-Boubbou, K., Kamat, M., Chen, J., Li, W., & Huang, X. (2012). Development of Multifunctional Hyaluronan-Coated Nanoparticles for Imaging and Drug Delivery to Cancer Cells. *Biomacromolecules,* 13(4), 1144-1151.

Fleige, E., Quadir, M. A., & Haag, R. (2012). Stimuli-responsive polymeric nanocarriers for the controlled transport of active compounds: Concepts and applications. *Advanced Drug Delivery Reviews,* 64(9), 866-884.

Huang, G., Chen, H., Dong, Y., Luo, X., Yu, H., Moore, Z., Bey, E. A., Boothman, D. A., & Gao, J. (2013). Superparamagnetic iron oxide nanoparticles: amplifying ROS stress to improve anticancer drug efficacy. *Theranostics,* 3(2), 116-126.

Laurent, S., Dutz, S., Hafeli, U. O., & Mahmoudi, M. (2011). Magnetic fluid hyperthermia: focus on superparamagnetic iron oxide nanoparticles. *Advances in Colloid and Interface Science,* 166(1-2), 8-23.

Li, M., Kim, H. S., Tian, L., Yu, M. K., Jon, S., & Moon, W. K. (2012). Comparison of Two Ultrasmall Superparamagnetic Iron Oxides on Cytotoxicity and MR Imaging of Tumors. *Theranostics,* 2(1), 76-85.

Maeda, H. (2001). The enhanced permeability and retention (EPR) effect in tumor vasculature: the key role of tumor-selective macromolecular drug targeting. *Advances in Enzyme Regulation,* 41(1), 189-207.

Ruoslahti, E., Bhatia, S. N., & Sailor, M. J. (2010). Targeting of drugs and nanoparticles to tumors. *The Journal of Cell Biology,* 188(6), 759-768.

EXAMPLES

Figure 1:
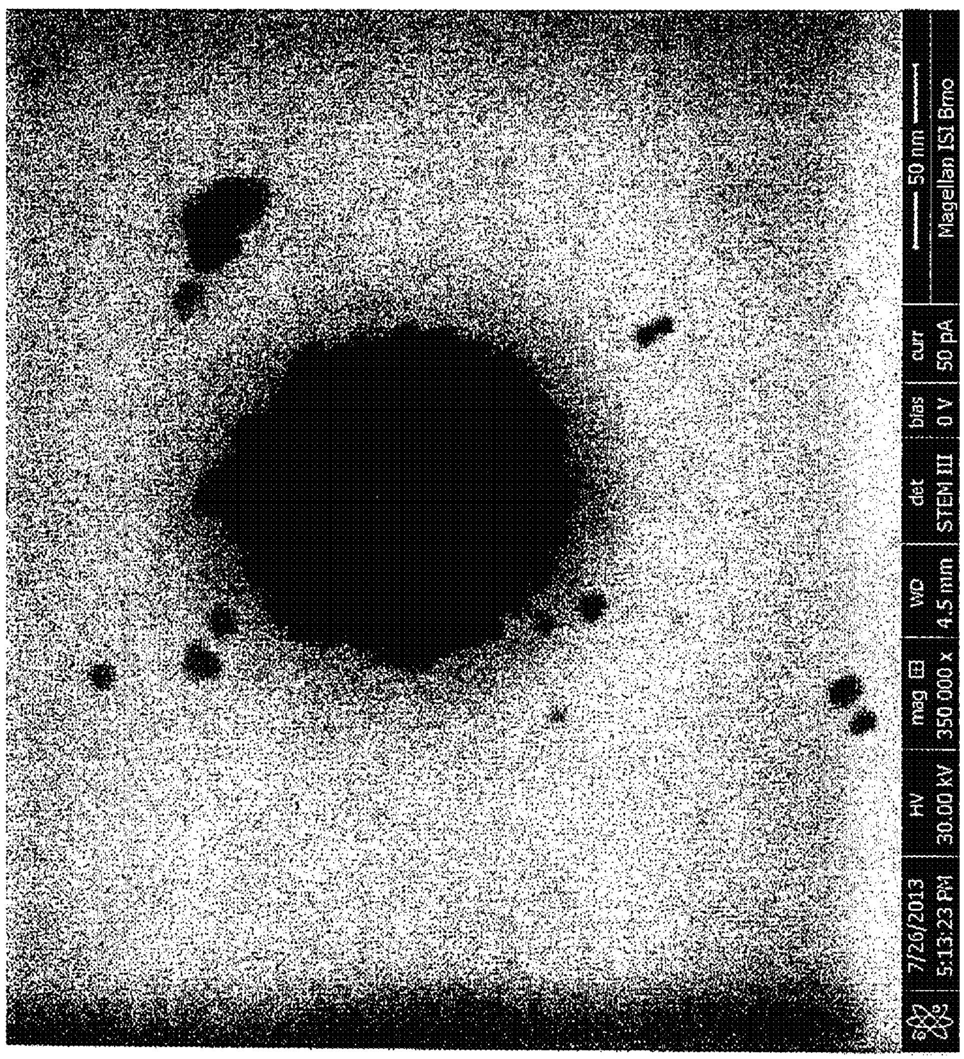
FIG. 1. TEM photo of nanoparticles (SPIONs) encapsulated in hydrophobized hyaluronan.

*SS*=substitution degree=100%*molar amount of the bound substitute/molar amount of all polysaccharide dimers The term equivalent (eq) used herein relates to a hyaluronic acid dimer, if not indicated otherwise. The percentages are weight percents, if not indicated otherwise.

Molecular weight of hyaluronic acid (source: Contipro Pharma, a.s., Dolní Dobrouě, CZ) was determined by SEC-MALLS.

The term inorganic nanoparticles means inorganic nanoparticles having a diagnostic function, where the diagnostic function is an essential common property of inorganic nanoparticles used in the composition according to the invention. The diagnostic function is intended to mean the possibility to detect said particles by methods available in medicine. SPIONs may be detected by means of magnetic resonance and ZnO and upconversion nanoparticles by means of luminiscence imaging, and all these particles are just optimised for detection, and that's why they are used. Therefore, out of a set of inorganic nanoparticles, those were selected that allow for the detection (of micelles) in vivo or in vitro.

The term upconversion nanoparticles is to mean upconversion lanthanide nanoparticles, i.e. nanoparticles containing elements from the group of rare earths, since no other inorganic nanoparticles capable of an effective upconversion of energy are known.

Example 1 Preparation of Hydrophobized Hyaluronic Acid, More Specifically the Oleyl Derivative (C18:1) of Hyaluronic Acid by Means of Mixed Anhydride of Benzoic Acid and Oleic Acid 100 g of sodium hyaluronan (250 mmol, 15 kDa) were dissolved in 2000 ml of demi water. Then 1000 ml of isopropanol were gradually added. Thereafter, TEA (70 ml, 3 eq.) and DMAP (1.52 g, 0.05 eq.) were added to the solution. At the same time, oleic acid (35.3 g 0.5 eq) was dissolved in 1000 ml of isopropanol, then TEA (70 ml, 3 eq.) and benzoyl chloride (14.4 ml, 0.5 eq.) were added to the solution. After the activation of the acid the precipitate was filtered off into the prepared HA solution. The reaction proceeded for 3 hours at room temperature. Then the reaction mixture was diluted by 1000 ml of demi water with an addition of 95 g of NaCl. The acylated derivative was isolated from the reaction mixture by precipitation by using a quadruple of absolute isopropanol. After decantation, the precipitate was repeatedly washed with an aqueous solution of isopropanol (85% vol.).

SS 13% (determined from NMR).

$^1$H NMR ($D_2O$): δ 0.88 (t, 3H, —$CH_2$—$C\underline{H}_3$), δ 1.22-1.35 (m, 20H, (—$CH_2$—$)_{10}$), δ 1.60 (m, 2H, —$C\underline{H}_2$—$CH_2$—CO—), δ 2.0 (4H, (—$CH_2$—$)_2$), δ 2.41 (t, 2H, —$CH_2$—CO—), δ 5.41 (d, 2H, CH═CH)

This example describes a general method of synthesis of a hydrophobized derivative of hyaluronan. However, the procedure is not limited to the oleyl derivative only. A detailed disclosure of the synthesis of hydrophobized derivatives is mentioned in the patent application No. CZ PV2012-842.

Example 2. Preparation of SPIONs Having an Average Size of 5 nm 1.80 g of ferric oleate, 0.35 ml of oleic acid and 13.35 ml of 1-octadecene were added into a three-necked flask having the volume of 50 ml. The mixture was slowly heated under vacuum to 100° C., where it was maintained for 30 minutes for drawing away the volatile components. Then the mixture was heated under a mild argon flow to 280° C. and it was maintained at this temperature for 60 minutes. The mixture was bubbled through with argon during the reaction at 280° C. After cooling down to the room temperature, acetone was added to the reaction mixture and the nanoparticles were separated by centrifugation. The precipitated SPIONs were thereafter washed 4 times with a mixture of hexane/acetone (the ratio successively 1:4 to 1:1) and finally, they were dispersed in toluene and stored at 4° C. in dark.

Yield: 78%

Size of the nanoparticles: 5.2 t 0.8 nm (according to the photo from the electron microscope)

Example 3. Preparation of SPIONs Having an Average Size of 10 nm 1.80 g of ferric oleate, 0.35 ml of oleic acid and 13.35 ml of 1-octadecene were added into a three-necked flask having the volume of 50 ml. The mixture was slowly heated under vacuum to 100° C., where it was maintained for 30 minutes for drawing away the volatile components. Then the mixture was heated under a mild argon flow to the boiling point (~317° C.) and it was maintained at this temperature for 60 minutes. After cooling down to the room temperature, the SPIONs were separated in the same way as in Example 2.

Yield: 74%

Size of the nanoparticles: 9.8±0.5 nm (according to the photo from the electron microscope)

Example 4. Preparation of SPIONs Having an Average Size of 20 nm 1.80 g of ferric oleate, 0.35 ml of oleic acid and 5.34 ml of 1-octadecene and 6 g of n-docosane were added into a three-necked flask having the volume of 50 ml. The mixture was slowly heated under vacuum to 100° C., where it was maintained for 30 minutes for drawing away the volatile components. Then the mixture was heated under a mild argon flow to 315° C. and it was maintained at this temperature for 60 minutes. After cooling down to the room temperature, the SPIONs were separated in the same way as in Example 2.

Yield: 56%

Size of the nanoparticles: 21.1±3.1 nm (according to the photo from the electron microscope)

Example 5. Preparation of ZnO Nanoparticles

Zinc acetate dihydrate (1185.30 mg; 5.4 mmol) was introduced into a three-necked flask having the volume of 250 ml and dissolved in methanol (90 ml) at room temperature. Meanwhile, a solution of tetramethyl ammonium hydroxide (1622.91 mg; 8.96 mmol) in methanol (22.39 ml) was prepared in a two-necked flask. Both above mentioned solutions were degassed in an ultrasound bath while being bubbled through with argon for 15 minutes (the temperature of the aqueous bath 50° C., output 120 W). The methanol solution of zinc acetate was heated under reflux in an oil bath (the bath temperature 60° C.). After the addition of oleic acid (310 μl; 0.99 mmol) the mixture was brought to the boiling point (bath temperature 85° C.). The solution of tetramethyl ammonium hydroxide in methanol was heated under reflux (bath temperature 75° C.) and quickly added into the three-necked flask containing zinc acetate and oleic acid. The reaction mixture was refluxed while being constantly stirred (600 rpm) and bubbled through with argon for 2 minutes (bath temperature 85° C.). Then the mixture was diluted by methanol (90 ml) and cooled for 15 min on an ice bath. The cooled mixture was centrifuged for 15 min (4000×g, 4° C.). The particles were washed with ethanol (3×25 ml), each washing step was followed by centrifugation for 10 minutes (4000×g, 25° C.). The particles were dispersed in chloroform (45 ml) and stored at 4° C. in dark.

Quantum efficiency of fluorescence: 34% (determined by a relative method, standard=norharman)

Size of the nanoparticles: 3.4±0.3 nm (according to the photo from the electron microscope)

Example 6. Preparation of Upconversion Nanoparticles

The molar amounts corresponding to 1.60 mmol of yttrium (III) acetate, 0.36 mmol of ytterbium (III) acetate and 0.04 mmol of erbium (III) acetate were introduced into a three-necked flask having the volume of 100 ml and octadec-1-en (34 ml) and oleic acid (12.0 ml) were added. The mixture was evacuated while being stirred hard (600 rpm) and it was slowly heated on an oil bath to 80° C. At this temperature, the mixture was stirred in vacuum until total clarification and from that moment for further 90 minutes. The flask with the mixture was filled with argon and after cooling down to the room temperature in an argon atmosphere a solution of NaOH (200 mg) and $NF_4F$ (296.3 mg) in methanol (20 ml) was added, whereupon the mixture became cloudy immediately. The mixture was stirred at room temperature overnight, then methanol was slowly evaporated at 65° C. (oil bath). Then the flask with the mixture was transferred to a heating mantle controlled by a PID-controller. The mixture was gradually introduced to vacuum, in vacuum it was slowly heated to 112° C. and at this temperature it was being degassed for 30 minutes. Then the flask containing the mixture was filled with argon and under air reflux it was heated to 305° C. in a mild argon flow at speed of 2° C./min. At 305° C. the mixture was left for 110 minutes, after removing the heating it cooled down naturally to the room temperature.

The upconversion nanoparticles were precipitated from the reaction mixture by ethanol (a double volume of the reaction mixture volume) and then isolated by centrifugation (RCF 3000× g; 10 minutes). The nanoparticles (sediment) were dispersed in hexane (5 ml), precipitated by ethanol (10 ml) and separated by means of centrifugation (RCF 3000× g; 7 minutes). The nanoparticles were purified in this manner three times by the hexane/ethanol system and three times by the hexane/acetone system. Finally, the nanoparticles were dispersed in chloroform (10 ml) and stored at room temperature.

Nanoparticles composition (ICP-OES):$NaYF_4$:Yb/Er (80 mol. % Y, 18 mol. % Yb, 2 mol. % Er Organic component fraction (TGA): 7%

Size of the nanoparticles (electron microscope): 34±2 nm

Example 7. Preparation of the Composition of a Capronyl Derivative of Hyaluronic Acid (HAC6) with SPIONs 150 mg of acylated derivative of hyaluronan (HAC6, DS=60%, Mw=38 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.1% (wt.)

Example 8. Preparation of the Composition of a Caprylyl Derivative of Hyaluronic Acid (HAC8) with SPIONs 150 mg of acylated derivative of hyaluronan (HAC8, DS=22%, Mw=20 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.1% (wt.)

Example 9. Preparation of the Composition of a Caprinyl Derivative of Hyaluronic Acid (HAC10) with SPIONs 150 mg of acylated derivative of hyaluronan (HAC10, DS=15%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.2% (wt.)

Example 10. Preparation of the Composition of a Palmitoyl Derivative of Hyaluronic Acid (HAC16) with SPIONs 150 mg of acylated derivative of hyaluronan (HAC16, DS=9%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.2% (wt.)

Example 11. Preparation of the Composition of a Stearyl Derivative of Hyaluronic Acid (HAC18) with SPIONs 150 mg of acylated derivative of hyaluronan (HAC18:0, DS=9%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.0% (wt.)

Example 12. Preparation of the Composition of an Oleyl Derivative of Hyaluronic Acid (HAC18:1) with SPIONs 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.0% (wt.)

The morphology of the clustered nanoparticles in the polymeric micelle is shown in FIG. 1.

Example 13. Preparation of the Composition of an Oleyl Derivative of Hyaluronic Acid (HAC18:1) with SPIONs 120 mg of acylated derivative of hyaluronan (HAC18:1, DS=12%, Mw=15 kDa) prepared according to Example 1 was being dissolved for 2 hours in 12 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 7.25 mg of SPIONs dispersed in 4 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.8% (wt.)

Example 14. Preparation of the Composition of Linoleyl Derivative of Hyaluronic Acid (HAC18:2) with SPIONs 150 mg of acylated derivative of hyaluronan (HAC18:2, DS=12%, Mw=15 kDa) prepared according to Example 1 was being dissolved for 4 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 0.98% (wt.)

Example 15. Preparation of the Composition of a Linolenyl Derivative of Hyaluronic Acid (HAC18:3) with SPIONs 150 mg of acylated derivative of hyaluronan (HAC18:3, DS=3%, Mw=15 kDa) prepared according to Example 1 was being dissolved for 4 hours in 15 ml of demi water at constant stirring on a magnetic stirrer. The SPIONs (stabilized by oleic acid, size of the nanoparticles: 5 nm), prepared according to Example 2, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.0% (wt.)

Example 16. Preparation of the Composition of an Oleyl Derivative of Hyaluronic Acid (HAC18:1) with SPIONs 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 10 nm), prepared according to Example 3, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 0.4% (wt.)

Example 17. Preparation of the Composition of an Oleyl Derivative of Hyaluronic Acid (HAC18:1) with SPIONs 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer. The SPIONs (stabilized by oleic acid, size of the nanoparticles: 20 nm), prepared according to Example 4, were transferred from the toluene medium to the chloroform medium.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Fe (ICP determination): 1.7% (wt.)

Example 18. Preparation of the Composition of an Oleyl Derivative of Hyaluronic Acid (HAC18:1) with SPIONs and Paclitaxel 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer. Then 5 mg of SPIONs (stabilized by oleic acid, size of the nanoparticles: 5 nm), prepared according to Example 2, were transferred from toluene to chloroform. The nanoparticles prepared in this way were mixed with 6 mg of paclitaxel dissolved in 3 ml of chloroform.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of SPIONs with 6 mg of paclitaxel in $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles and paclitaxel were separated by means of repeated centrifugation (3×4500 RPM, 10 min) and the resulting supernatant containing nanomicelles of hyaluronan with the loaded nanoparticles and paclitaxel was taken away, filtered through a 1.0 μm glass filter and lyophilised.

The amount of the loaded Fe (ICP determination): 1.5% (wt.)

The amount of the loaded PTX (HPLC determination): 0.3% (wt.)

Example 19. Preparation of the Composition of an Oleyl Derivative of Hyaluronic Acid (HAC18:1) with ZnO Nanoparticles 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of ZnO (from Example 5) dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Zn (ICP determination): 1.6% (wt.)

Example 20. Preparation of the Composition of an Oleyl Derivative of Hyaluronic Acid (HAC18:1) with Upconversion Nanoparticles 150 mg of acylated derivative of hyaluronan (HAC18:1, DS=12%, Mw=15 kDa) prepared according to Example 1 was being dissolved for 2 hours in 15 ml of demi water at constant stirring on a magnetic stirrer.

The solution of acylated hyaluronan was transferred into a rosette sonication vessel (RZ 1, volume: 25 ml), immersed in an ice bath. First the solution was sonicated for 60 s (sonication parameters: 200 W, amplitude 65%, cycle 0.5 s and sonotrode S2). Further, 5 mg of upconversion nanoparticles (from Example 6) dispersed in 3 ml of $CHCl_3$ were gradually added to said solution (sonication parameters: 200 W, amplitude 85%, cycle 0.8 s and sonotrode S2). The homogenized suspension was further sonicated for 15 min (sonication parameters: amplitude 65%, cycle 0.5 s and sonotrode S2). The free nanoparticles were separated by means of repeated centrifugation (3×4500 RPM, 10 min) and the resulting supernatant containing nanomicelles of hyaluronan with the loaded nanoparticles was taken away, filtered through a 1.0 μm glass filter and lyophilised.

The amount of the loaded Er; Y; Yb (ICP determination): 0.02; 0.50; 0.19% (wt.)

Example 21. In Vitro Cytotoxicity of the Composition of an Acylated Hyaluronan with SPIONs Primary cells and non-tumor and tumor lines (Table 1) were seeded in 96-well panels and cultivated for 24 hours in 37° C./5% $CO_2$. Then the cells were treated with solutions of compositions of an acylated hyaluronan with SPION from Examples 7-12, 14 and 15 at concentrations 10, 100, 200 and 500 μg/ml (concentration of polymeric micelles in the culture medium). At the same time, the viability of the acylated hyaluronan alone and of SPIONs alone was measured (in the respective concentrations). The viability of the cells was monitored in times 0, 24, 48 and 72 h by means of the MTT method and the resulting values indicate the inhibition or activation of the cell viability in the given time point. Inhibition of the cell viability of cells treated with compositions of various acylated HA derivatives with SPIONs (FIGS. 2A-C) and the influence of the composition HAC18:1+SPIONs (from Example 12) on various tumor lines (FIG. 3) was monitored. FIGS. 4A-C show the comparison of the cytotoxic action of the composition (according to Example 12, 16, 17) with 5, 10 and 20 nm SPIONs. The cell lines are described in Table 1.

TABLE 1

List of the tested adherent cell lines.

| Designation of the cell line | Cell type/origin |
|---|---|
| Control line | |
| NHDF | Primary human dermal fibroblasts |
| 3T3 | mouse fibroblast line |
| Tumor line | |
| HT29 | human colorectal adenocarcinoma |
| A2058 | human melanoma |
| A549 | human lung carcinoma |
| C3A | human hepatocellular carcinoma |
| MCF7 | human breast adenocarcinoma |
| HCT116 | human colorectal carcinoma |
| MDA-MB231 | human breast adenocarcinoma |
| Caco2 | human colorectal adenocarcinoma |

Figure 2A:
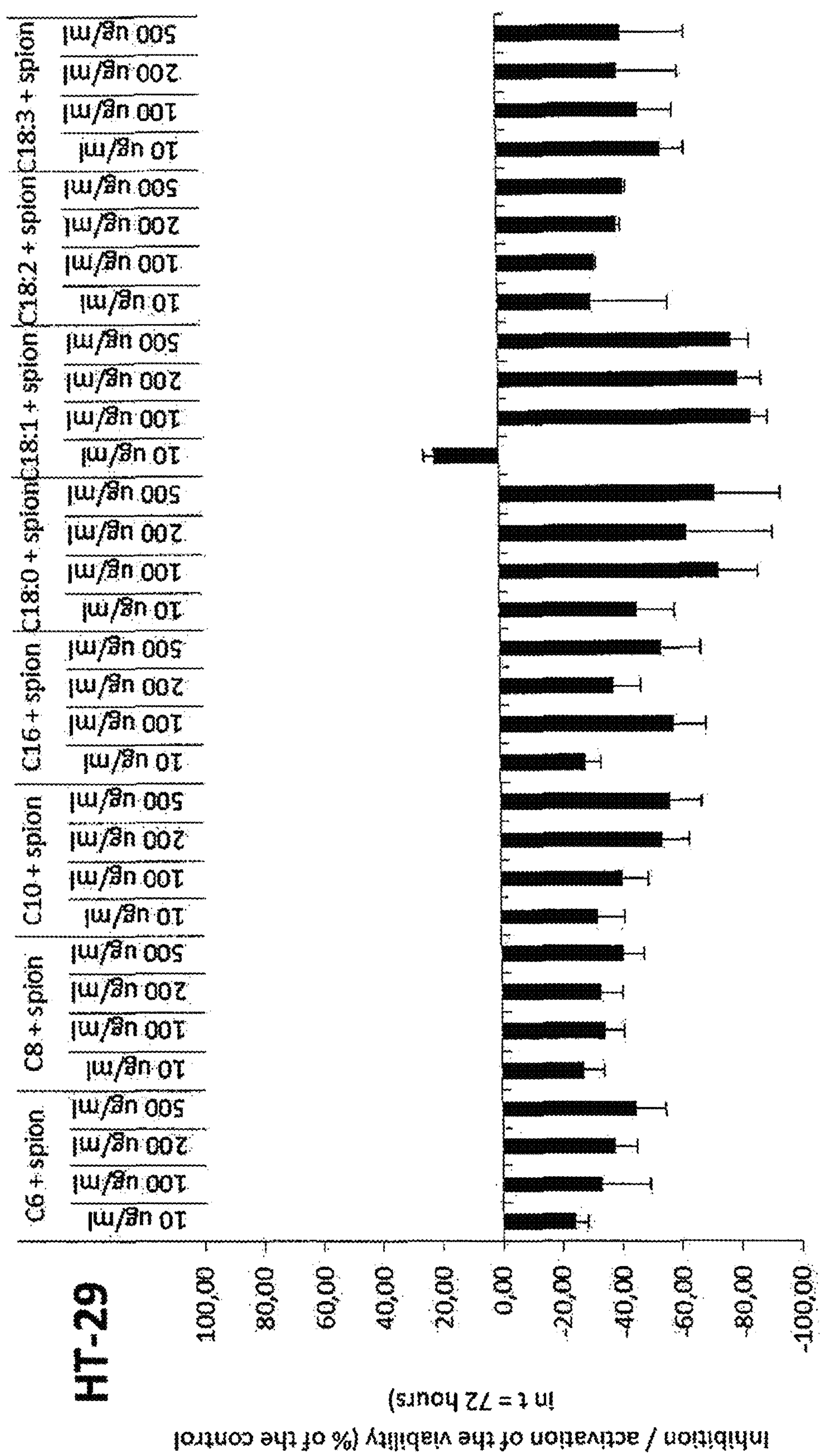
FIG. 2A, 2B, 2C. Inhibition of viability by the composition of acylated hyaluronan with SPIONs in tumor HT-29 line compared to the positive/neutral effect in control NHDF fibroblasts and a mouse non-tumor 3T3 line.
Figure 2B:
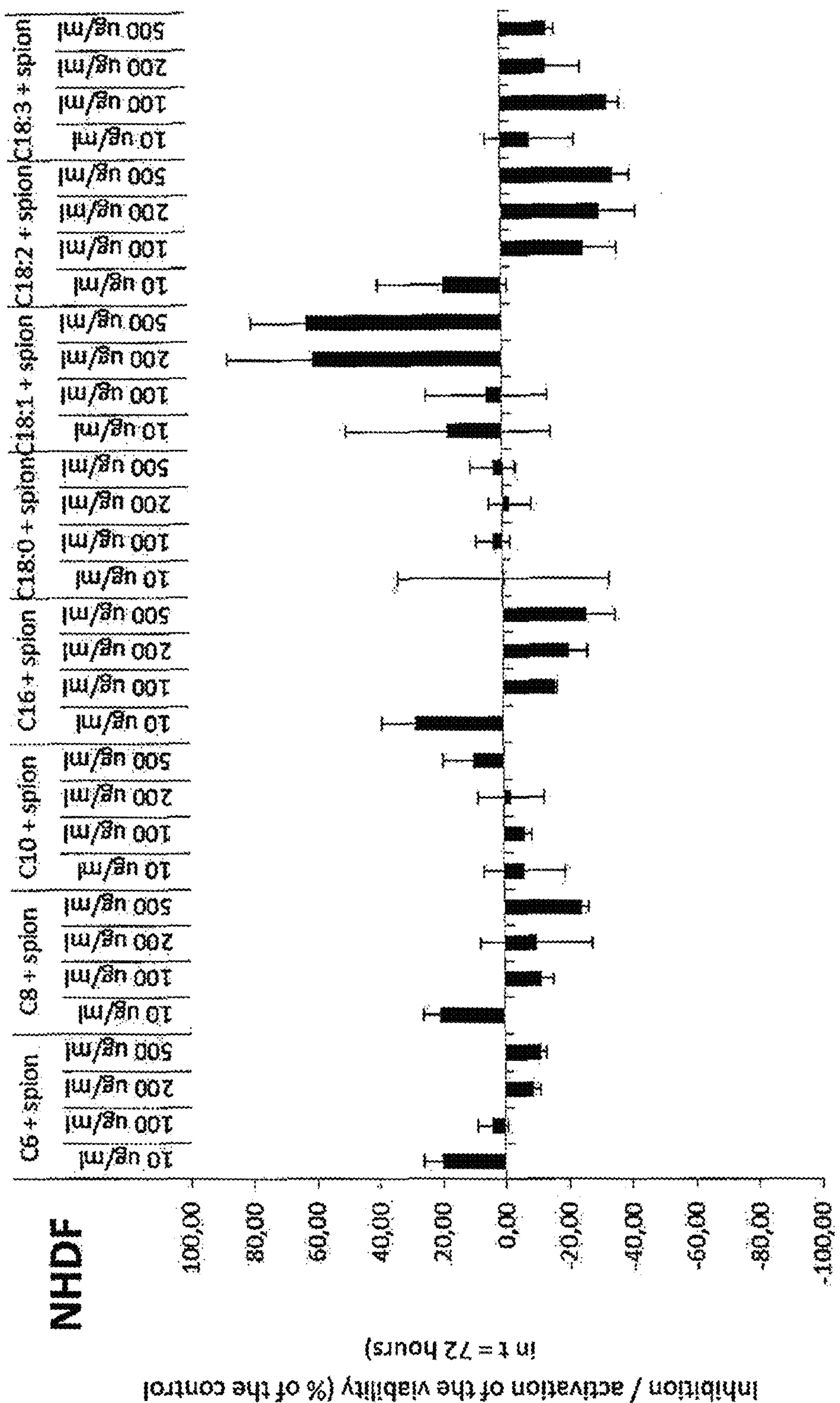
Figure 2C:
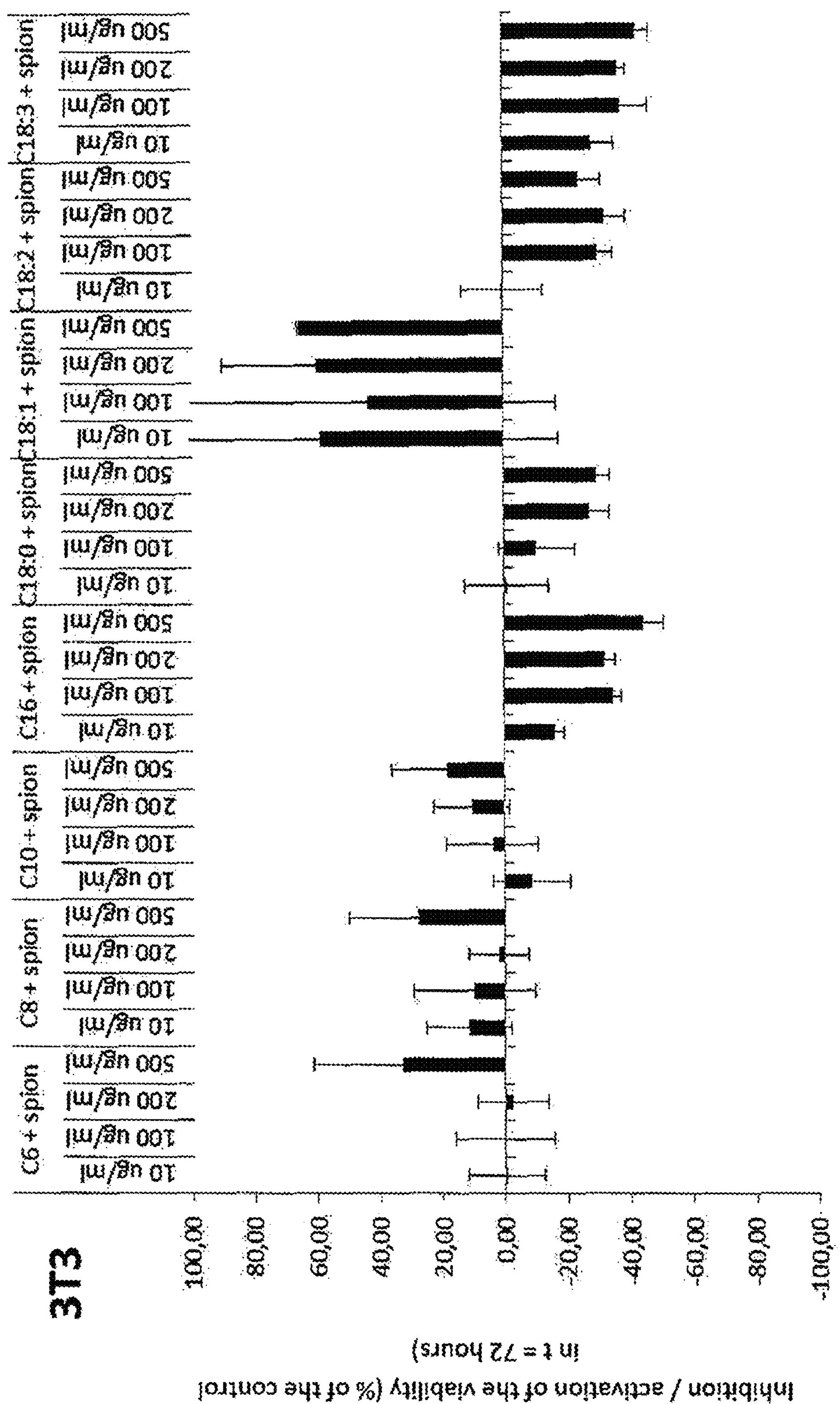

The results in FIGS. 2A-C show that unlike in control lines (NHDF and 3T3), in case of the tumor line HT29 there is a significant inhibition of the cell growth. The highest inhibitions were registered for the composition based on C18 and C18:1 acylated derivatives. The composition based on C18:1 derivatives with SPIONs even more supported the viability of NHDF and 3T3 cells. The acylated hyaluronan alone and the SPIONs did not influence the viability of any of the tested cells (data not shown).

Figure 3:
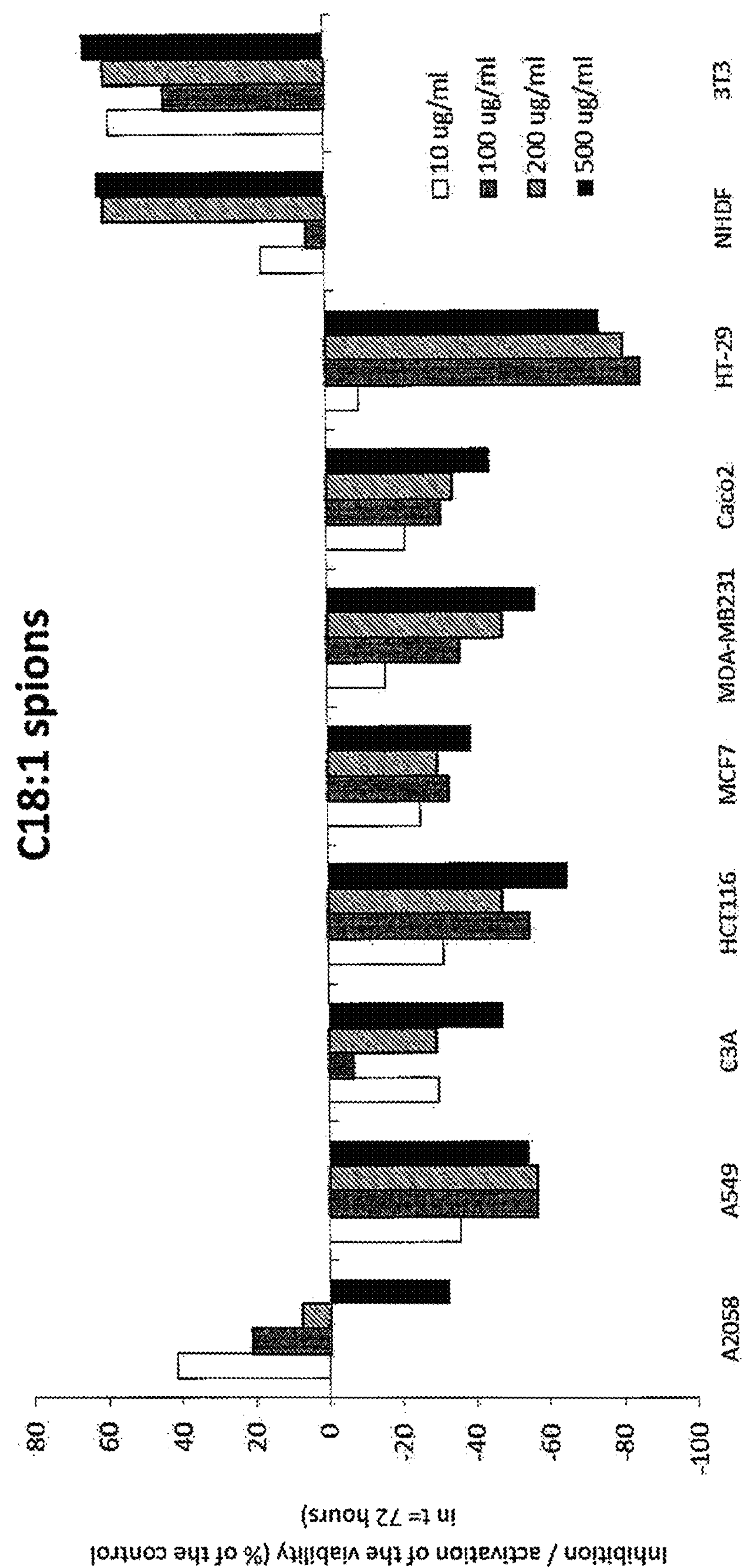
FIG. 3. Influence of the composition of acylated hyaluronan with SPIONs on the inhibition of viability of various tumor cell lines compared to the positive effect in control NHDF fibroblasts and a mouse non-tumor 3T3 line.
Figure 4A:
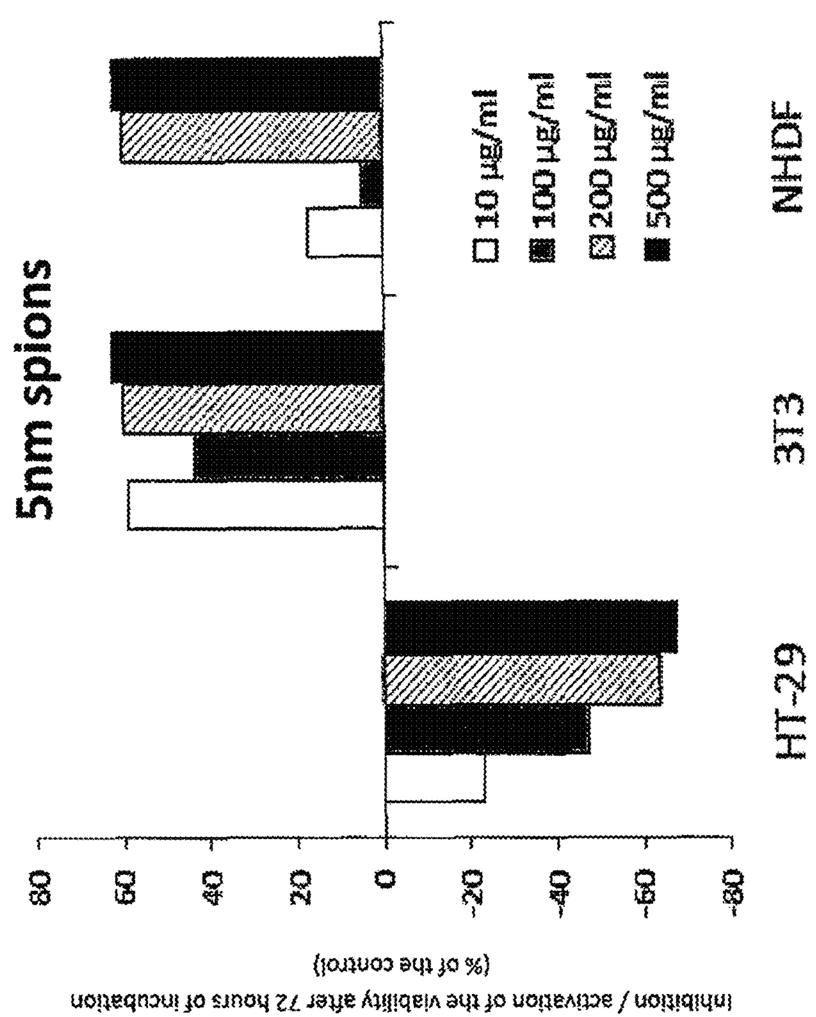
FIG. 4A, 4B, 4C. Comparison of the influence of the compositions of an acylated hyaluronan with encapsulated 5 nm, 10 nm a 20 nm SPIONs on the viability of the tumor cells HT-29 and the healthy NHDF and 3T3.
Figure 4B:
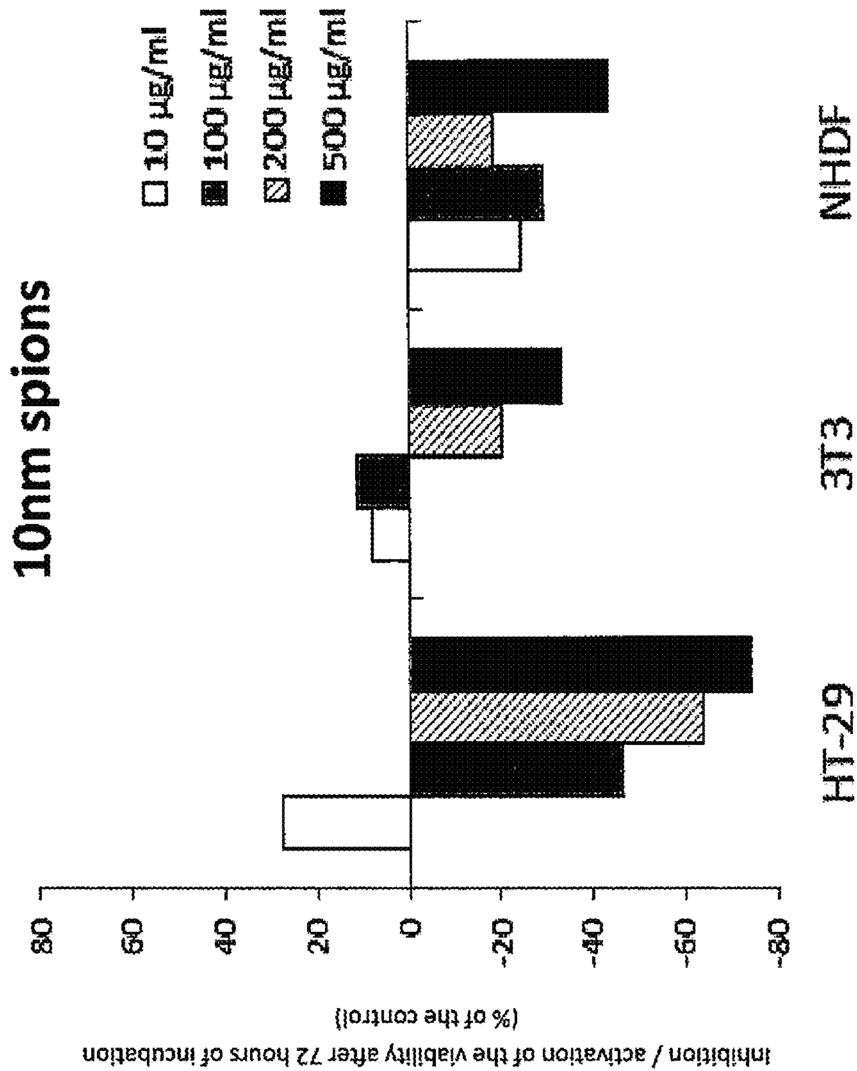
Figure 4C:
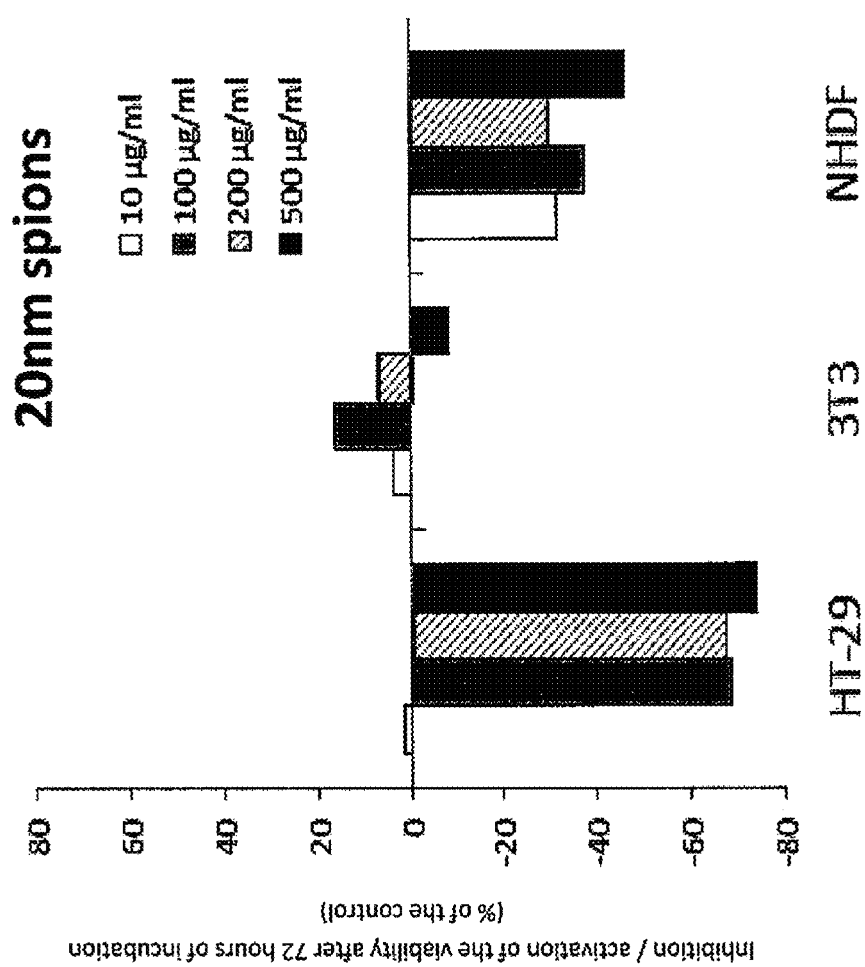

The composition of HAC18:1 with SPIONs was further used for treating other tumor lines (FIG. 3). The experimental data showed a slow-down of growth of tumor lines A549, HCT116, C3A, MCF7 and MDA-MB231 and Caco2. An exception was only the melanoma A2058 line where inhibition showed up only when treated with the highest concentration of the composition (500 μg/ml). The control fibroblasts (both NHDF and 3T3), in the contrary, were stimulated significantly by the composition and not even the highest concentration 500 μg/ml has shown any cytotoxic properties.

FIGS. 4A-C confirm the selective anti-tumor activity of the composition with 5 nm SPIONs. This effect is not observed to such an extent for compositions with 10 and 20 nm SPIONs.

Example 22. In Vitro Cytotoxicity of the Composition of an Acylated Hyaluronan with Nanoparticles of Zinc Oxide Primary human fibroblasts (NHDF), enteric tumor HT-29 cells and a mouse fibroblast 3T3 line were seeded to 96-well panels and cultivated for 24 hours in 37° C./5% $CO_2$. Then the cells were treated with solutions of compositions of an acylated hyaluronan with zinc oxide nanoparticles from Example 19 in concentrations 10, 100, 200 and 500 μg/ml (concentration of polymeric micelles). The viability of the cells was monitored in times 0, 24, 48 and 72 h by means of the MTT method and the resulting values indicate the inhibition or activation of the cell viability in the given time point (FIGS. 5A-C).

Figure 5A:
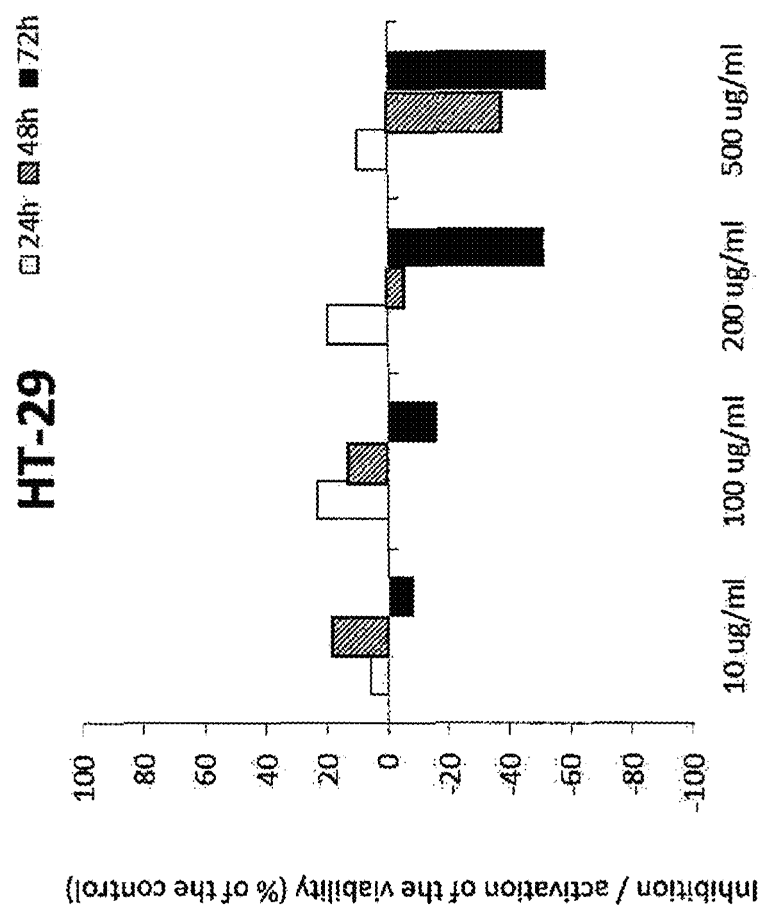
FIG. 5A, 5B, 5C. Inhibition of viability by means of the composition of an acylated hyaluronan with zinc nanoparticles in the tumor HT-29 line compared to the positive/neutral effect in control NHDF fibroblasts and a mouse non-tumor 3T3 line.
Figure 5B:
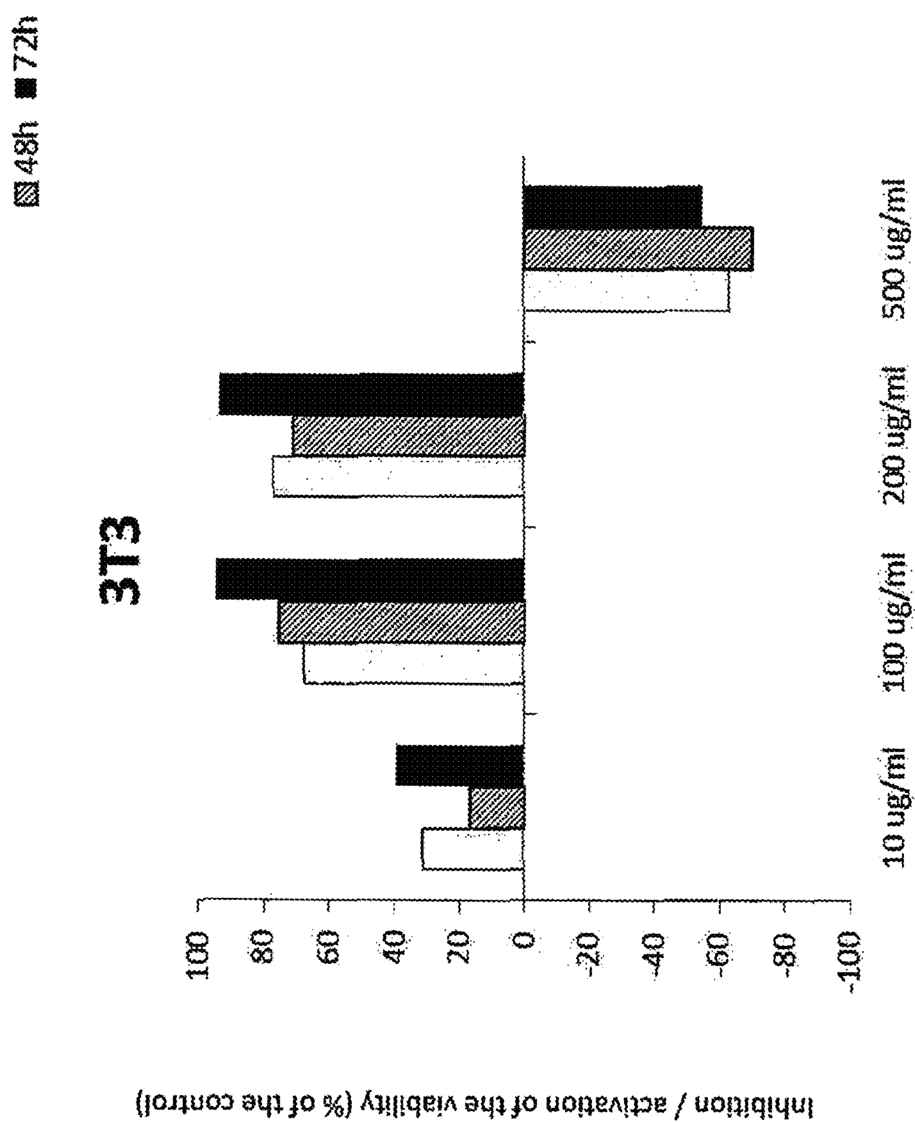
Figure 5C:
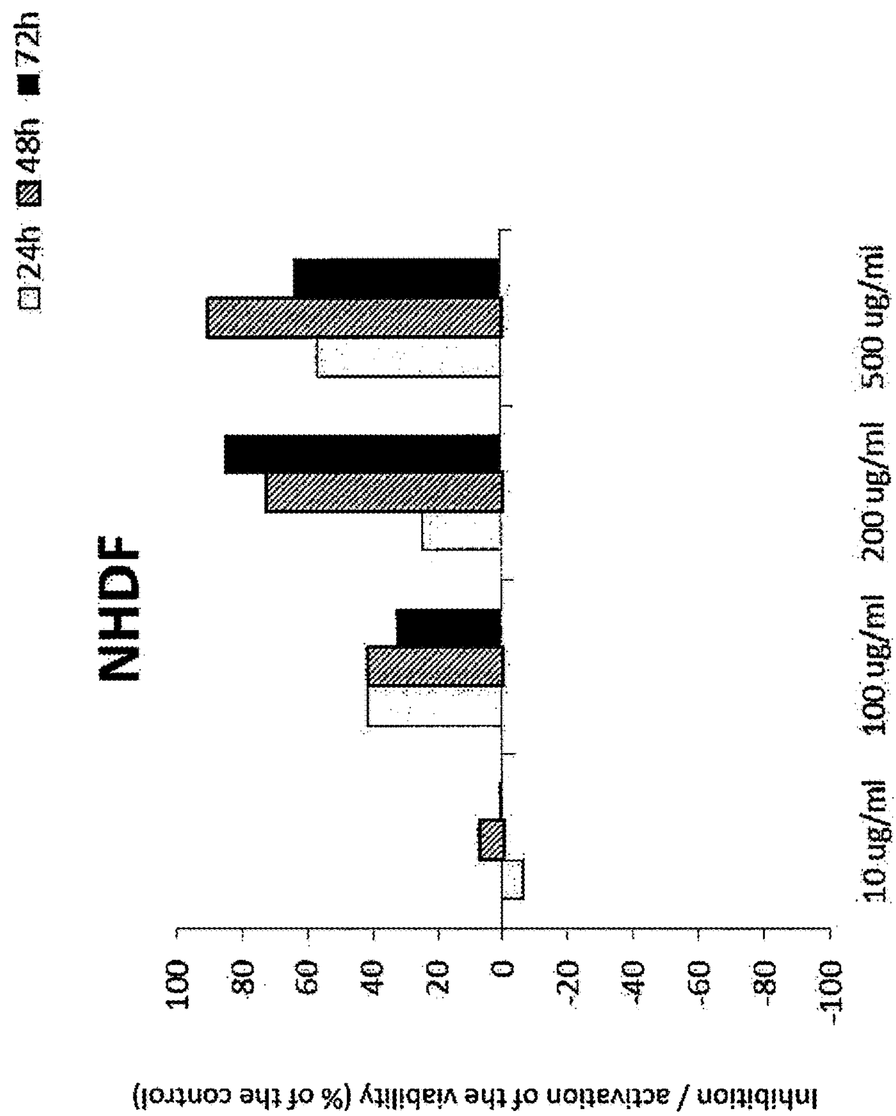

The results in FIGS. 5A-C show that unlike in control lines (NHDF and 3T3), with increasing incubation time and, further, in higher concentrations of polymeric micelles, inhibition of the tumor cell growth occurs. However, in this case, inhibition of the growth was also observed in case of concentration of 500 μg/ml in 3T3 cells. In lower concentrations of the composition and also in the control NHDF cell line, no inhibition has been observed.

Example 23. In Vitro Cytotoxicity of the Composition of an Acylated Hyaluronan with Upconversion Nanoparticles Primary human fibroblasts (NHDF), enteric tumor HT-29 cells and mouse fibroblast 3T3 line were seeded to 96-well panels and cultivated for 24 hours in 37° C./5% $CO_2$. Then the cells were treated with solutions of polymeric micelles with upconversion nanoparticles from Example 20 in concentrations 10, 100, 200 and 500 μg/ml (concentration of polymeric micelles). The viability of the cells was monitored in times 0, 24, 48 and 72 h by means of the MTT method and the resulting values indicate the inhibition or activation of the cell viability in the given time point (FIGS. 6A-C).

Figure 6A:
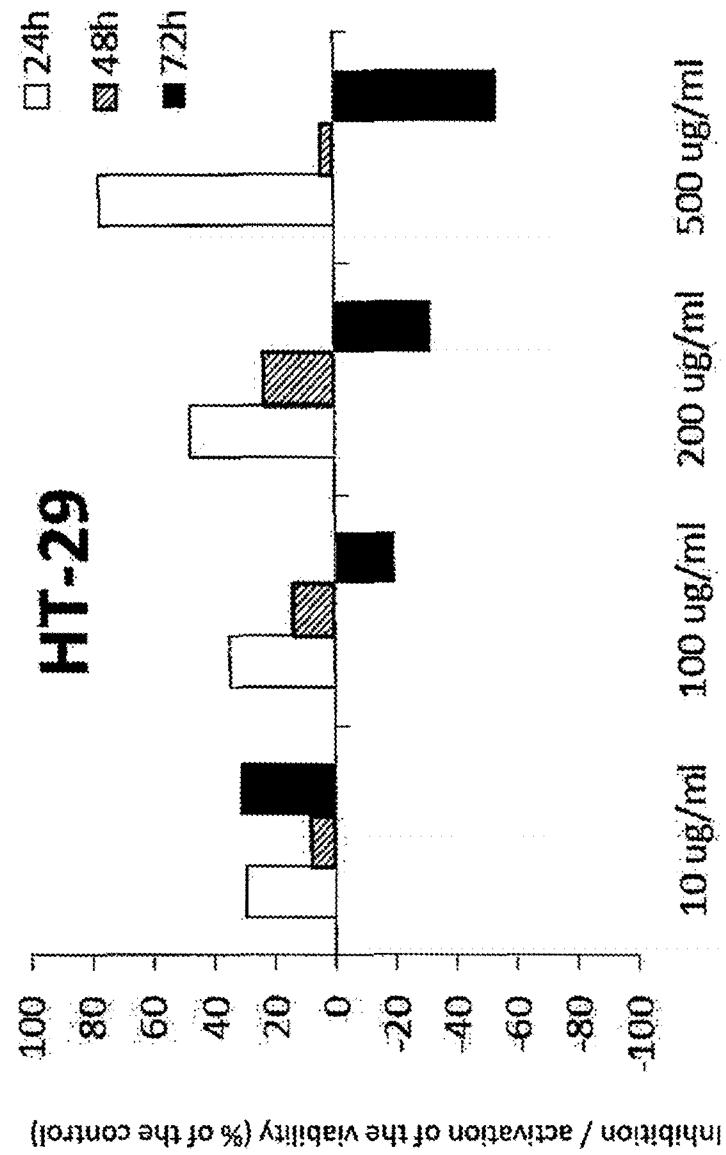
FIG. 6A, 6B, 6C. Inhibition of viability by means of the composition of an acylated hyaluronan with upconversion nanoparticles in the tumor HT-29 line compared to the positive/neutral effect in control NHDF fibroblasts and a mouse non-tumor 3T3 line.
Figure 6B:
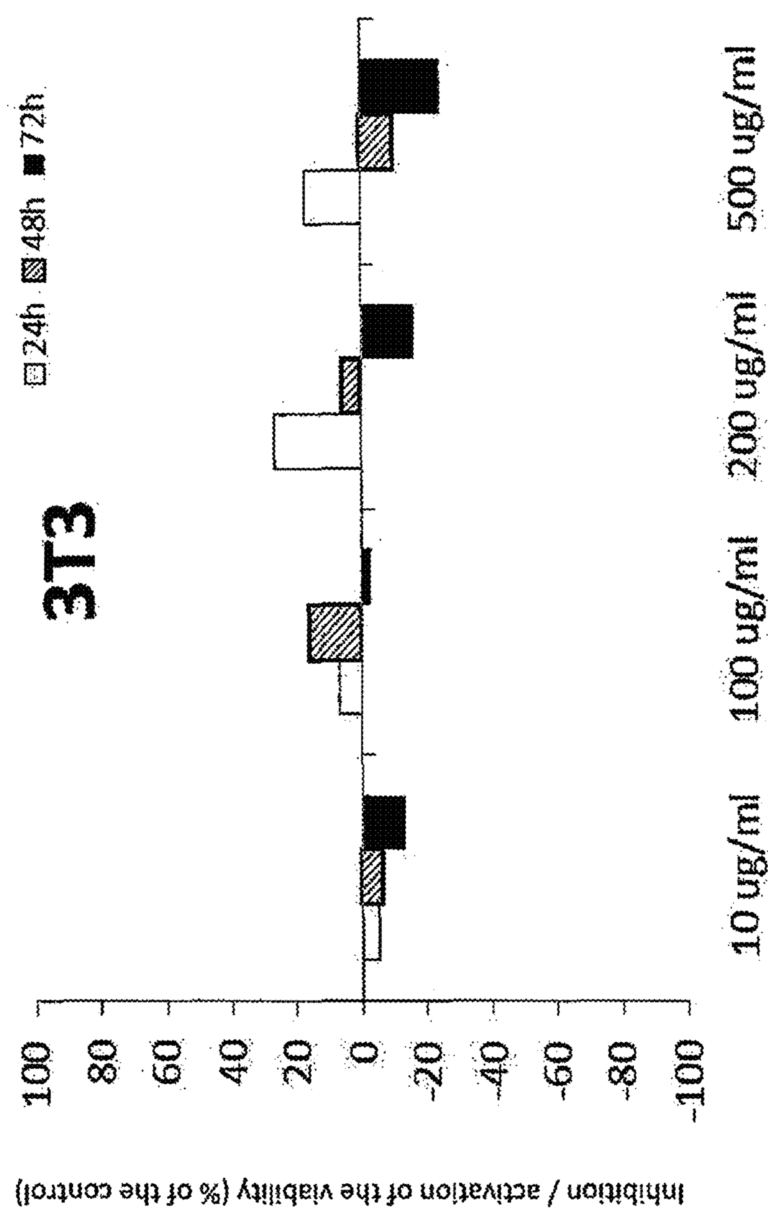
Figure 6C:
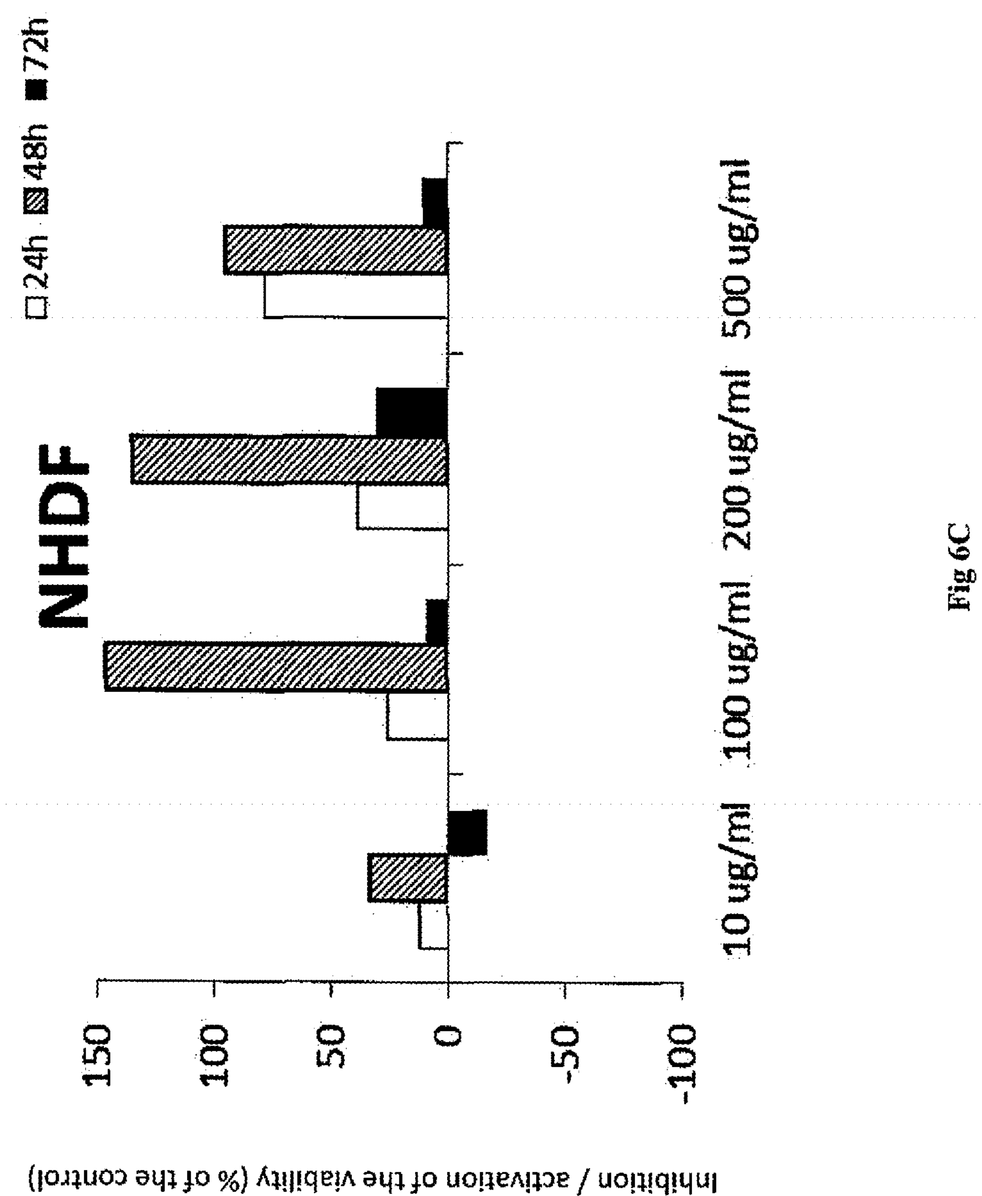

The results in FIGS. 6A-C show that unlike in control NHDF lines where the viability is highly increased, with increasing incubation time an inhibition of the tumor cell growth occurs. However, a slight inhibition is observed also in non-tumor 3T3 line.

Example 24. In Vitro Selective Cytotoxicity of the Composition of Acylated Hyaluronan with SPIONs Primary human fibroblasts labelled by DiO (green) and tumor HT-29 cells labelled by DiI (red) were in the ratio of 3:1 and the total concentration of 50.000 cells/well seeded into the wells of a 24-well panel in 1 ml of RPMI 1640 (Roswell Park Memorial Institut) medium. After achieving of min 80% confluence of the cell monolayer, the cells were treated with 200 μg/ml solution of the composition with SPIONs from Example 12. After 72 hours of incubation, a picture of the cells was taken by means of a fluorescence microscope Nikon Ti-Eclipse (FIG. 7).

Figure 8:
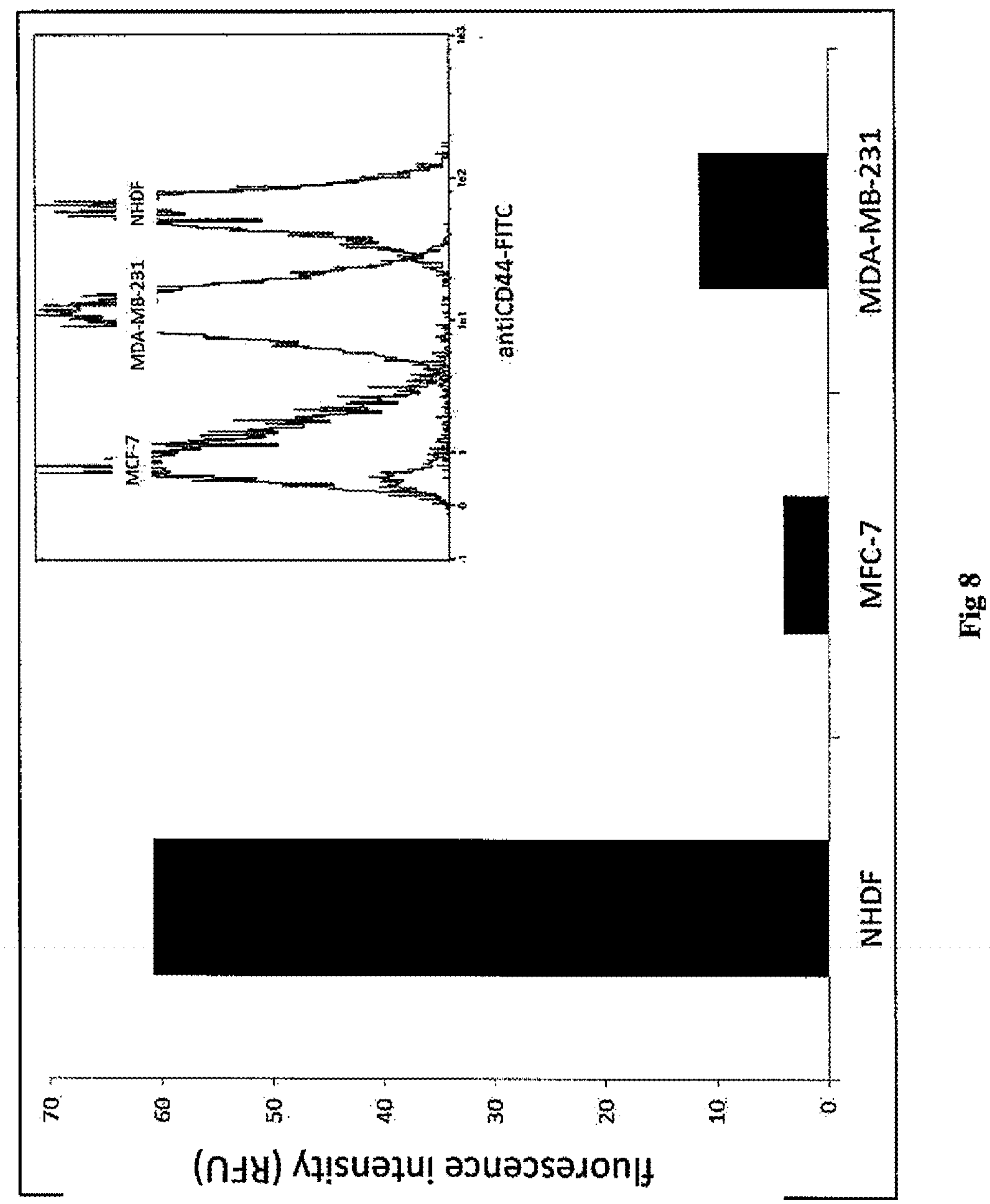
FIG. 8. Expression of the CD44 receptor on the surface of the cells NHDF, MCF-7 and MDA-MB-231 determined by means of flow cytometry.

For an explanation of the possible mechanism of the different activity towards the control cells and the tumor cells, expression of the CD44 receptor for hyaluronan was analysed by means of flow cytometry on NHDF, MCF-7 and MDA-MB-231 cells. After achieving the 80% confluence, the cells were washed with PBS, incubated for 15 min/RT with an antiCD44-FITC antibody, after the incubation they were 2× washed with PBS again and analysed on a flow cytometer MACSQuant Analyzer (Miltenyi Biotec). The results are indicated as fluorescence intensity (RFU) (FIG. 8).

Figure 9:
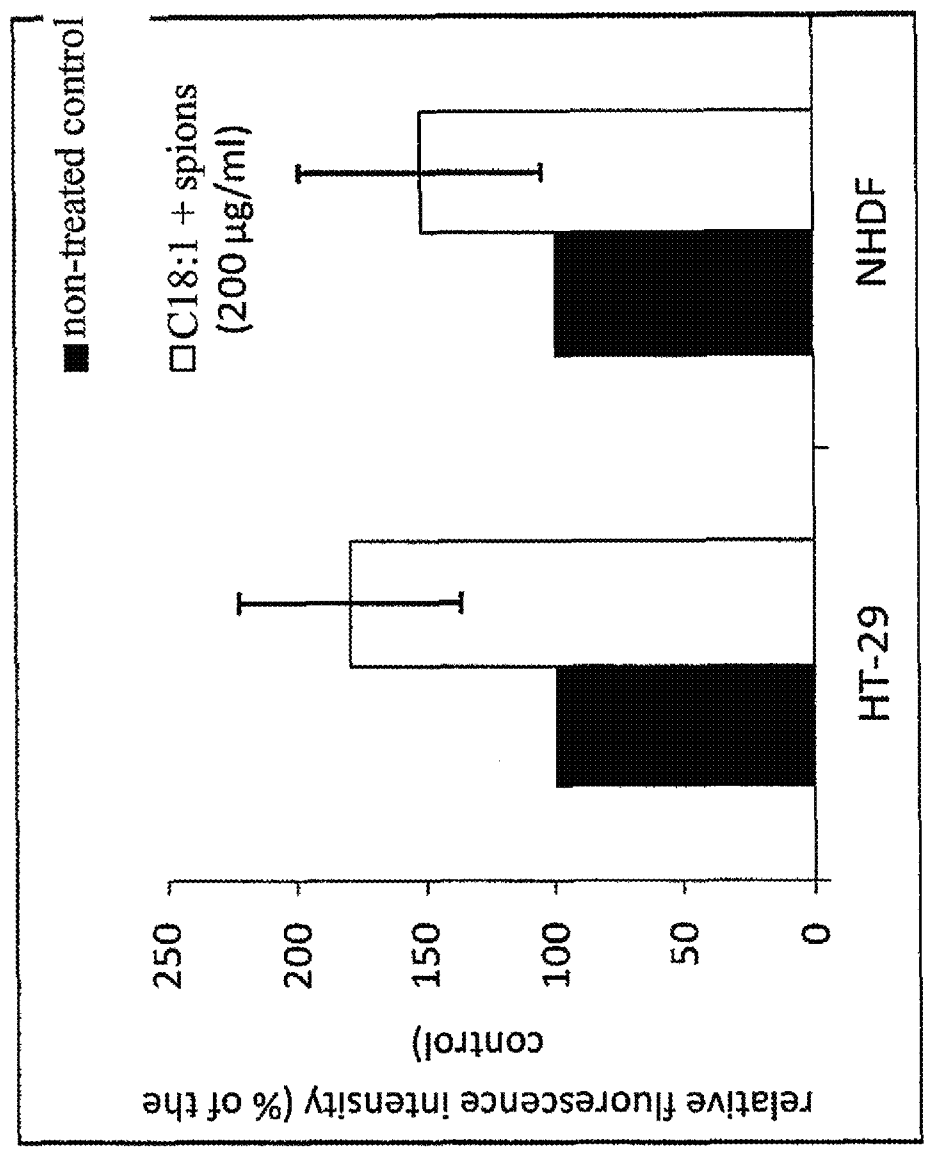
FIG. 9. Induction of the ROS formation by means of the composition of an acylated hyaluronan with SPIONs in NHDF and HT-29.

Moreover, for NHDF and HT-29 cells, oxidative stress was determined after the treatment with the composition of the acylated hyaluronan with SPIONs from Example 12. The cells were cultured on 6-well panels and after achieving the 80% confluence, they were treated with a 200 μg/ml solution of the composition with SPIONs for 24 hours. As far as the control cells are concerned, only the medium was exchanged for a fresh one without the content of the tested composition. After the incubation, the cells were washed and treated with DCF-DA (non-fluorescent substance which is oxidated by intracellular ROS to a fluorescent DCF, the final concentration: 1 uM) for 20 min/37° C./in dark. After the subsequent washing with PBS, the cells were analyzed on a flow cytometer MACSQuant Analyzer (Miltenyi Biotec). The results are indicated as the relative fluorescence intensity (% of the non-treated control) of DCF inside the cells (FIG. 9).

Figure 7:
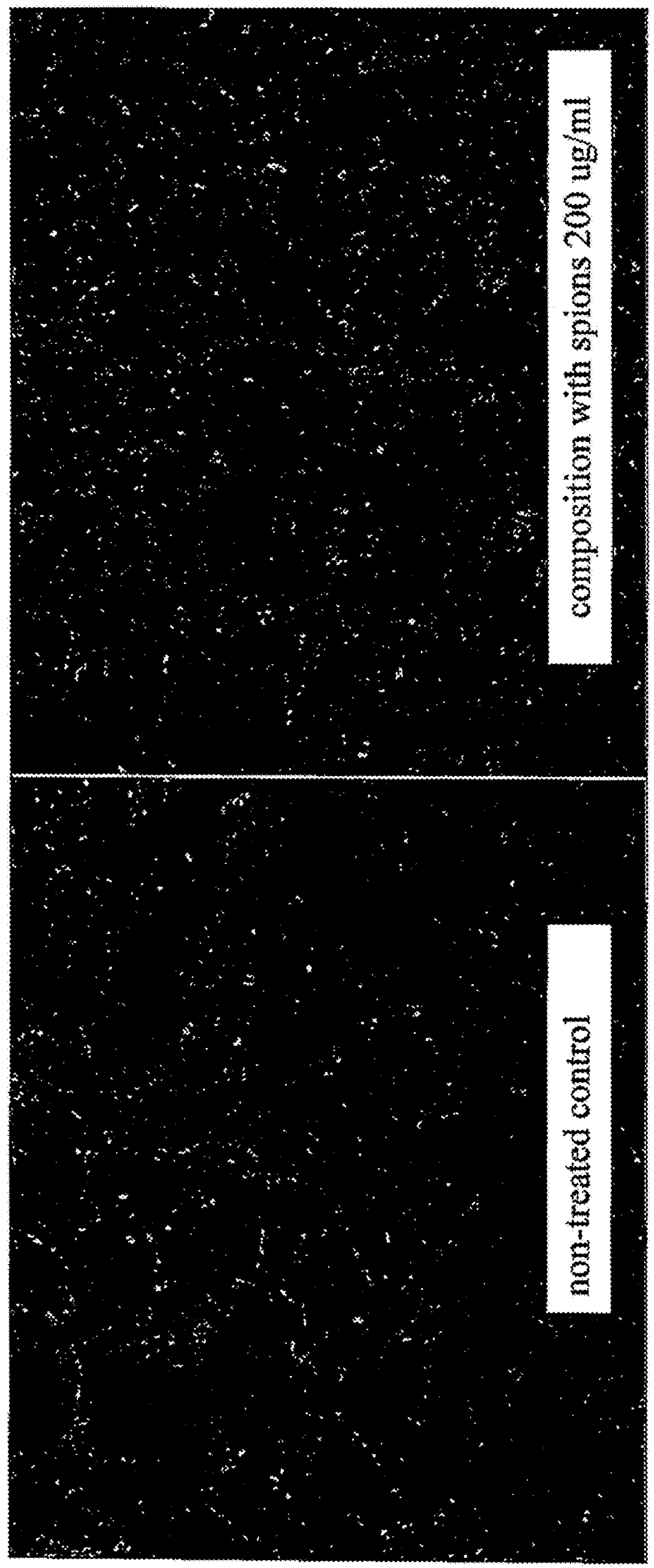
FIG. 7. Co-cultivation of healthy NHDF fibroblasts and control HT-29 cells with the composition of an acylated hyaluronan with SPIONs.

The results from FIG. 7 confirm the selective growth inhibition of the tumor HT-29 line, whereas the control fibroblasts NHDF are not influenced negatively and they reach the confluence. This effect is not caused by a different induction of ROS formation, said induction is increased in both types of cells but it is increased to the same level (FIG. 9). The explanation may be a different extent of response to said increase of the ROS production in NHDF and in HT-29 cells.

The difference of activity with respect to the control cells and to the tumor cells is not a function of expression of the main surface receptor for hyaluronan, CD44. FIG. 8 confirms a high expression of CD44 in control NHDF fibroblasts, the viability of which was increased by the composition, and a low expression in tumor MCF-7 and MDA-MB-231 lines, in which a significant viability inhibition was observed (FIG. 3).

Figure 10:
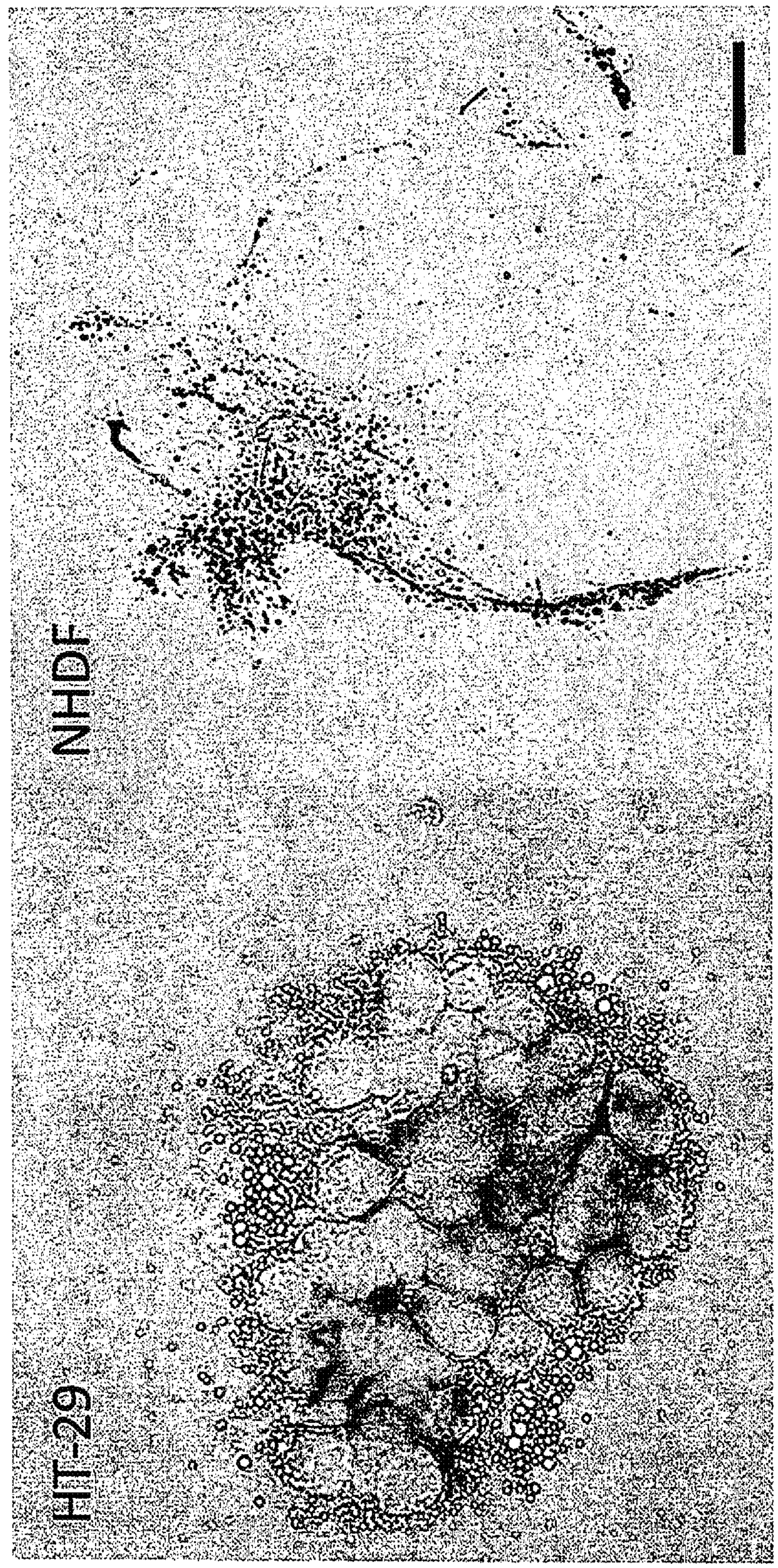
FIG. 10. Intracellular Fe staining in tumor HT-29 and control NHDF cells after incubation with the composition of an acylated hyaluronan with SPIONs (scale: 10 μm)

After staining of cells (detection of the presence of Fe by means of Prussian blue) incubated with the composition of the acylated hyaluronan with SPIONs from Example 12, a different Fe ion distribution is observed—while the dissolved Fe was detected in tumor cells, iron aggregates were detected in control cells (FIG. 10). This phenomenon could be the cause of the selective activity of the composition in tumor cells.

Example 25. Preparation of a Composition for an Intravenous Administration

650 μl of sterile 0.9% NaCl is added to 20-30 mg of the acylated hyaluronan with SPIONs from Example 12 prepared in a sterile manner, the solution is agitated from time to time until the total dissolution of the lyophilizate. The solution is injectable in vivo without problems.

The solution prepared in this way is stabile, as far as the hydrodynamic size of the particles is concerned, for at least 2 days.

Example 26. Preparation of a Composition for an Intravenous Administration

650 μl of sterile 5% dextrose is added to 20-30 mg of the acylated hyaluronan with SPIONs from Example 12 prepared in a sterile manner, the solution is agitated from time to time until the total dissolution of the lyophilizate. The solution is injectable in vivo without problems.

The solution prepared in this way is stabile, as far as the hydrodynamic size of the particles is concerned, for at least 2 days.

Example 27. In Vivo Detection of the Composition of an Acylated Hyaluronan with SPIONs Lewis Brown Norway rats with a glioblastoma tumor were used for in vivo testing. The tumors were inoculated by injecting a suspension of $3\times10^6$ glioblastoma cells into a muscle on a leg and 9 days after that the rats were administered intravenously the composition of acylated hyaluronan (HAC18:1) with SPIONs (750 μl of the solution in 0.9% NaCl, with the Fe content being 1.1 mg/kg). Then the rats were analyzed by means of Bruker Biospec (4.7 T).

Figure 11:
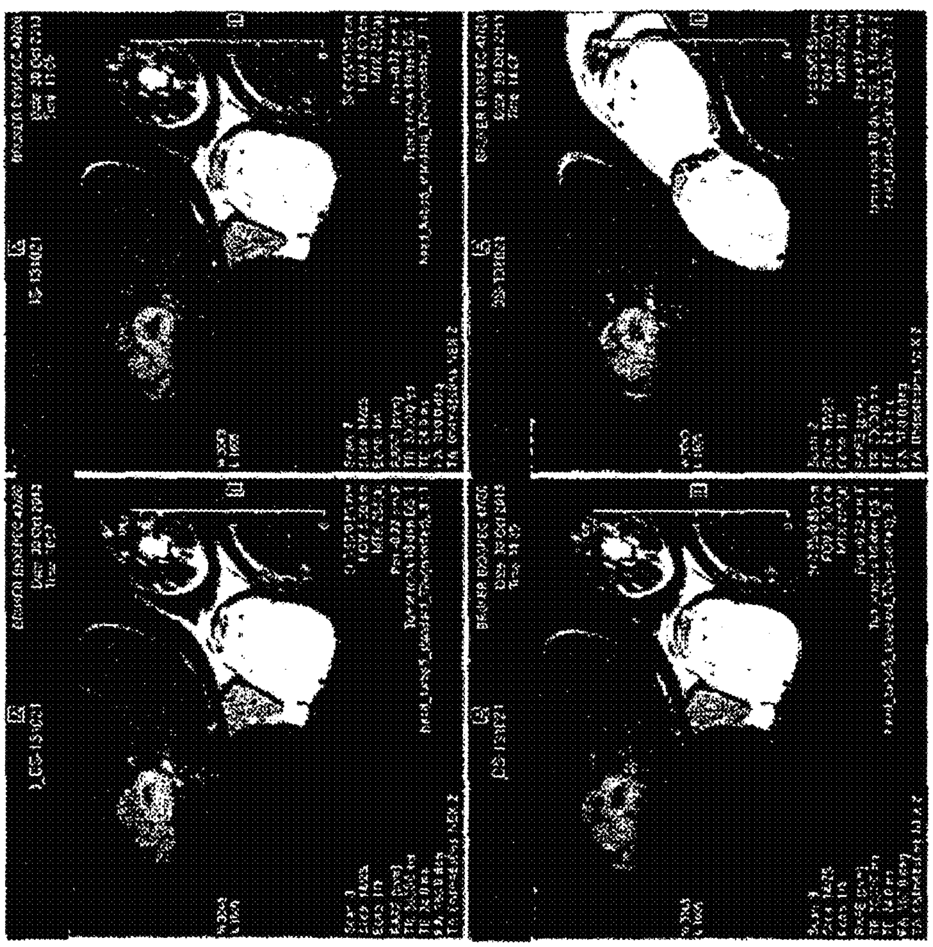
FIG. 11. MRI detection of time accumulation of SPIONs loaded in an acylated hyaluronan after an intravenous administration in a tumor (glioblastoma tumor, 1.1 mg Fe/kg).
Figure 12:
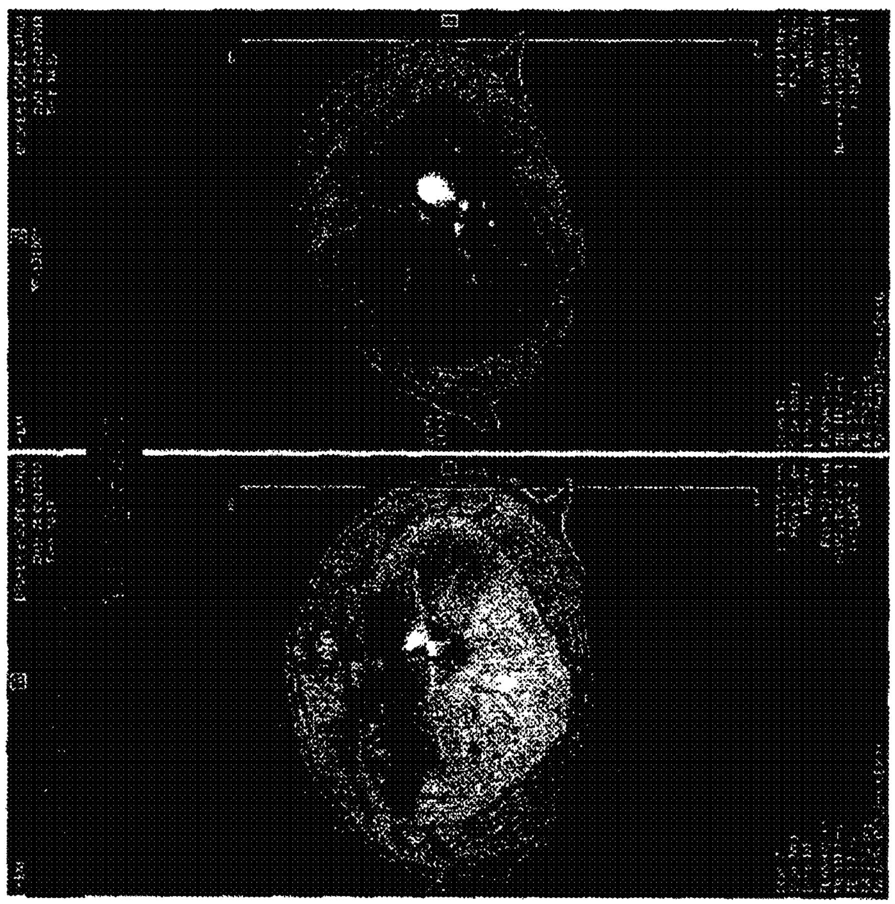
FIG. 12. MRI contrast of liver after an intravenous administration of the SPION composition loaded in an acylated hyaluronan (1.1 mg Fe/kg).

Accumulation of SPIONs in the tumor after the intravenous administration of the composition was confirmed in FIG. 11, where especially darkening of the edges of the tumor was detected. A visible accumulation of SPIONs was detected also in liver (FIG. 12), said composition therefore, can be used as a contrast agent for liver.

Figure 13:
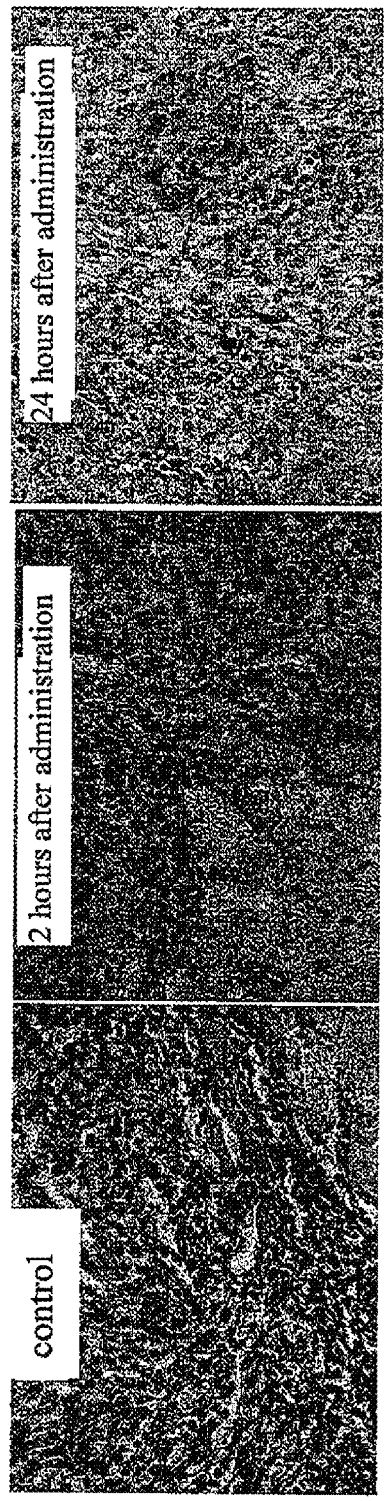
FIG. 13. Fe detection in histological sections of a tumor (2 and 24 hours upon administration of the SPION composition) after staining thereof by Prussian blue.
Figure 14:
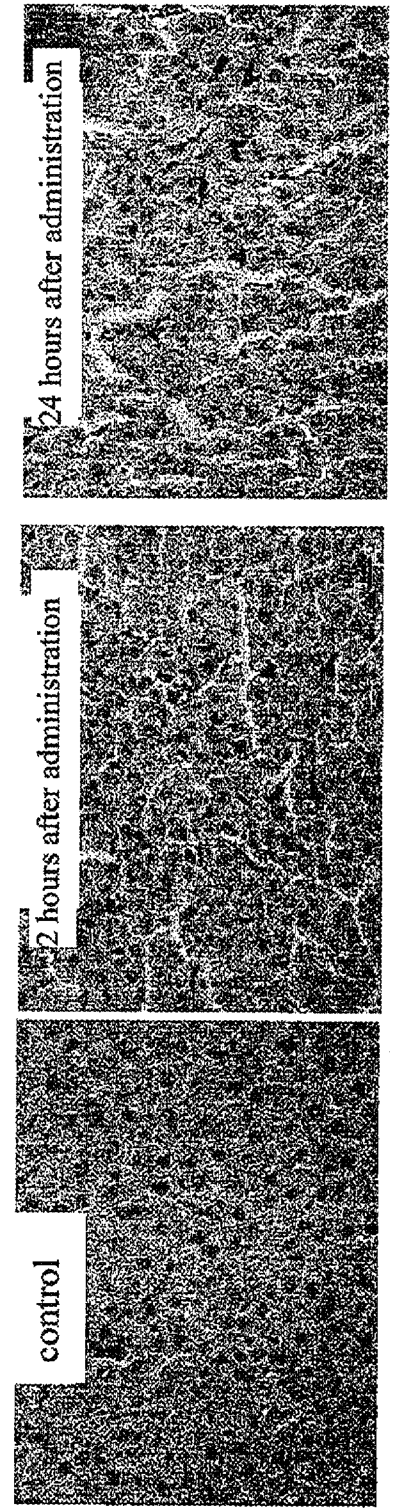
FIG. 14. Fe detection in histological sections of liver (2 and 24 hours upon administration of the SPION composition) after staining thereof by Prussian blue.

Accumulation of SPIONs was further confirmed after killing the animals on histological sections of the tumor (FIG. 13) and liver (FIG. 14), where the presence of Fe was detected by Prussian blue colouring (blue stains in Figures). The blue colouring was not detected in any of the control samples.

Example 28. Sterilization of the Composition of an Acylated Hyaluronan with SPIONs by Autoclaving Sterilization of the composition prepared according to Example 12 (concentration: 30 mg/ml in 0.9% NaCl) was carried out in an autoclave at 121° C. for 15 minutes.

Figure 15:
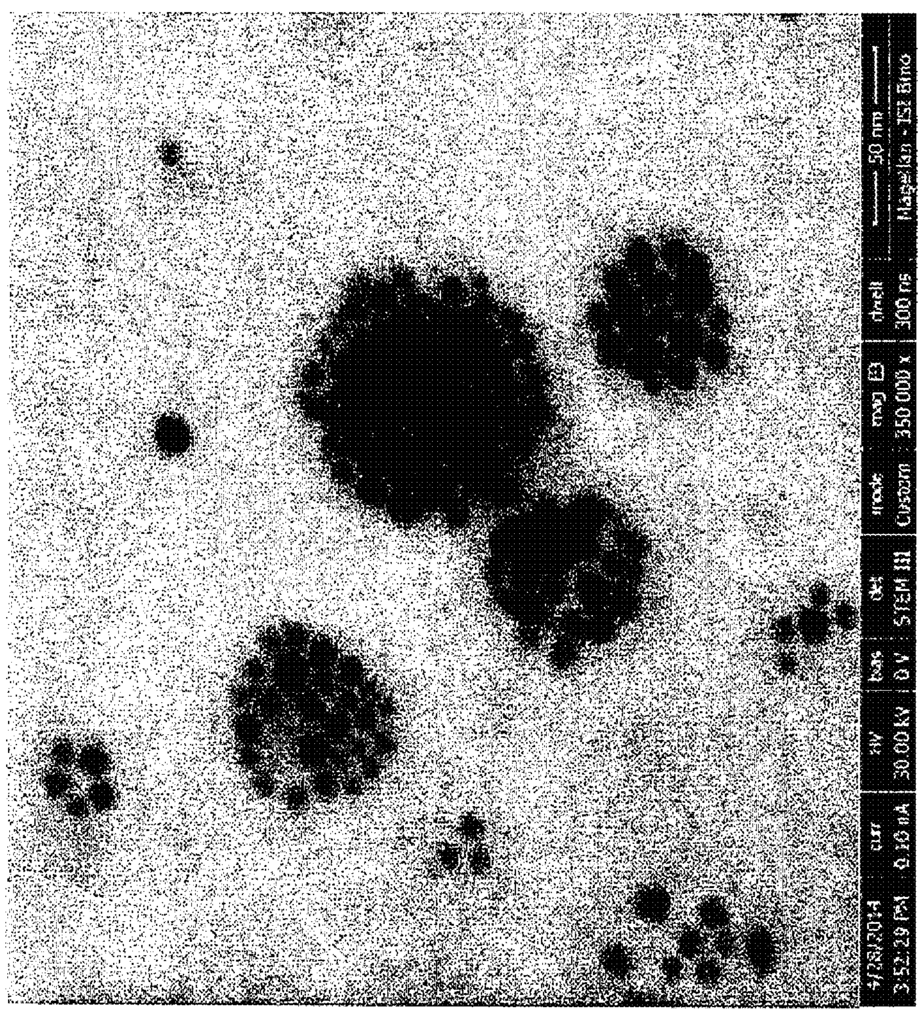
FIG. 15. TEM photo of nanoparticles (SPIONs) encapsulated in hydrophobized hyaluronan after sterilisation.

The solution was stabile after the sterilization, the SPIONs remained clustered in hyaluronan nanomicelles (FIG. 15), the selective cytotoxic effects with respect to the tumor cells were retained.

Figure 16:
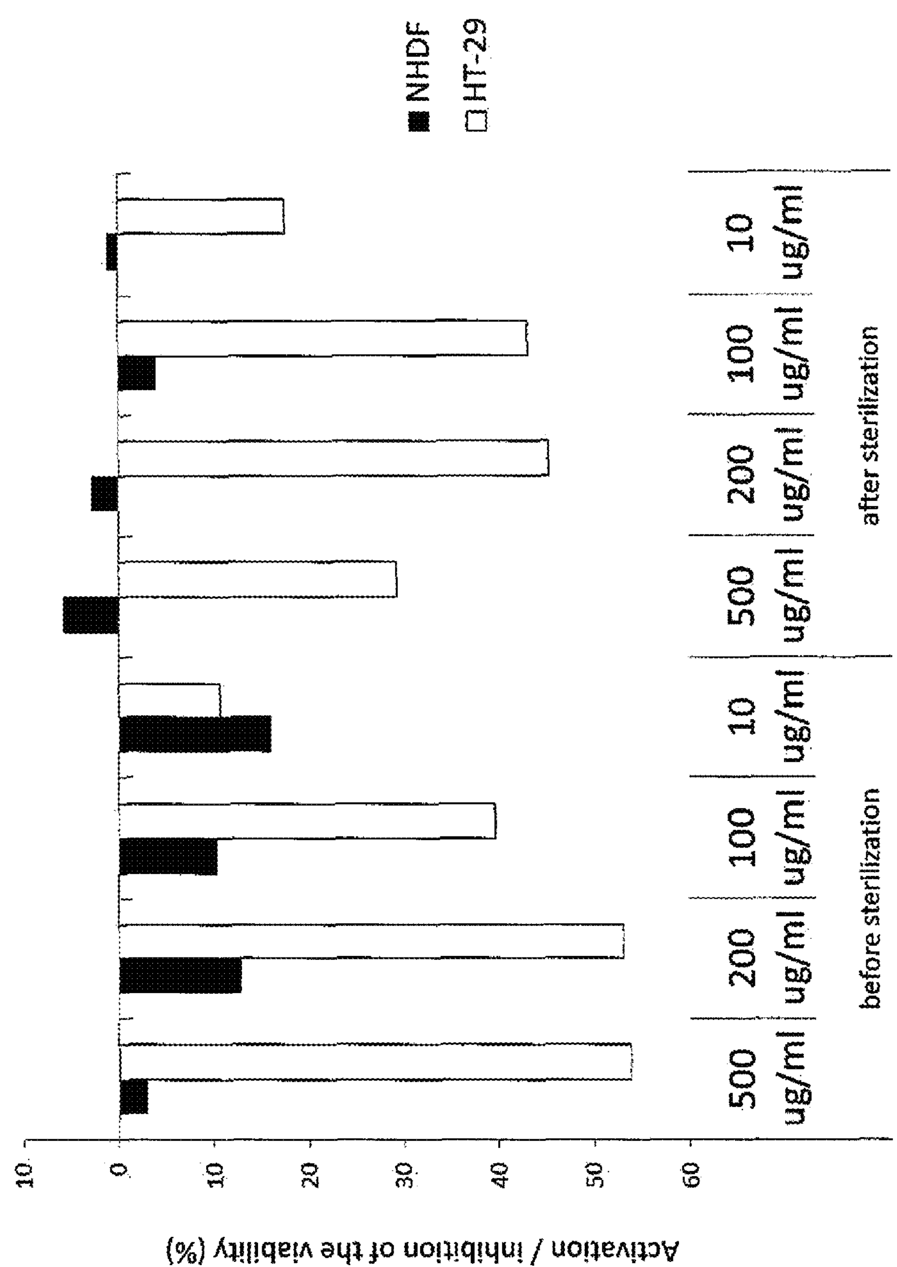
FIG. 16. Selective cytotoxicity of the SPION composition before and after sterilisation by autoclaving.

The cytotoxicity was determined on the tumor HT-29 line and control primary NHDF fibroblasts according to the procedure disclosed in Example 21. FIG. 16 shows a comparison of the composition from Example 12 before and after the sterilization by autoclaving, the selective cytotoxicity towards the tumor cells was retained even after the sterilization by autoclaving.

Example 29. Induction of Apoptosis in a Mouse Tumor Suspension Lymphoma EL4 Line The mouse lymphoma line EL4 (used for an induction of tumors in mouse experimental models of carcinogenesis) was cultured in the RPMI 1640 (Roswell Park Memorial Institut) medium. In the exponential phase of the growth, aliquots were prepared from the cell culture in the concentration of $5\times10^5$ cells/ml of the RPMI medium, which were treated with a 100, 200 and 500 μg/ml solution of the composition with SPIONs from Example 9. After 72 hours of incubation, the cells were washed and coloured specifically by means of fluorescent markers of the cell death (propidium iodide, AnnexinV-FITC), which were subsequently detected on a flow cytometer MACSQuant (Miltenyi Biotec).

Figure 17A:
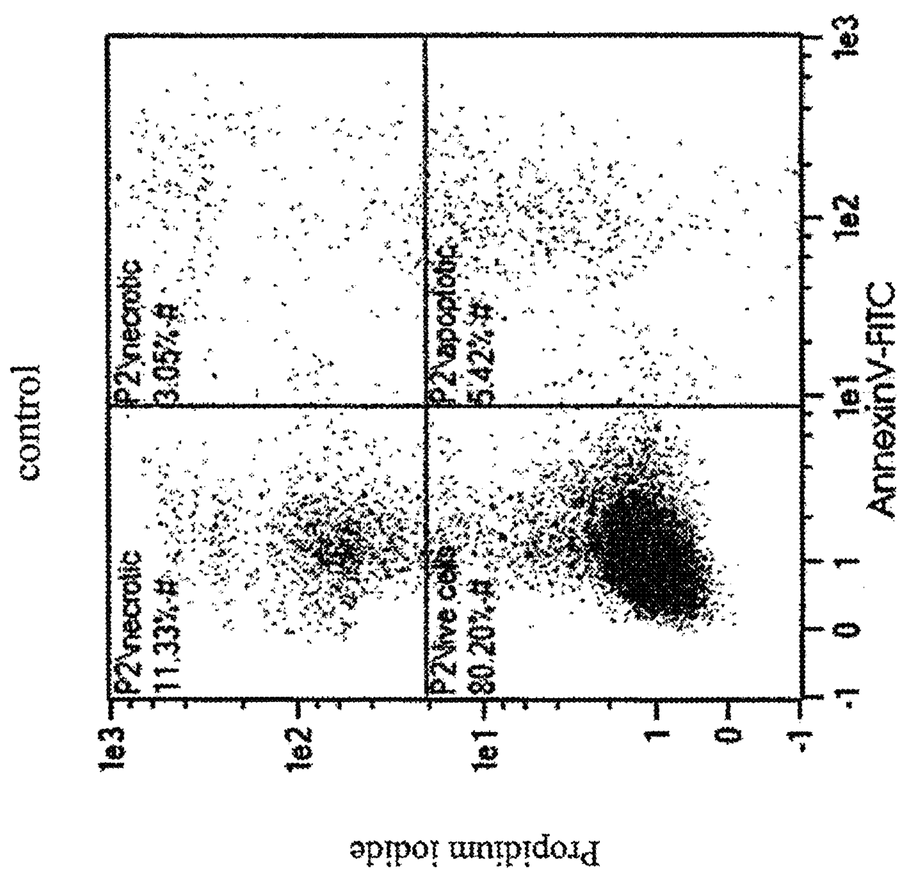
FIG. 17A, 17B, 17C. Induction of apoptosis by means of the SPION composition in a mouse tumor lymphoma line EL4.
Figure 17B:
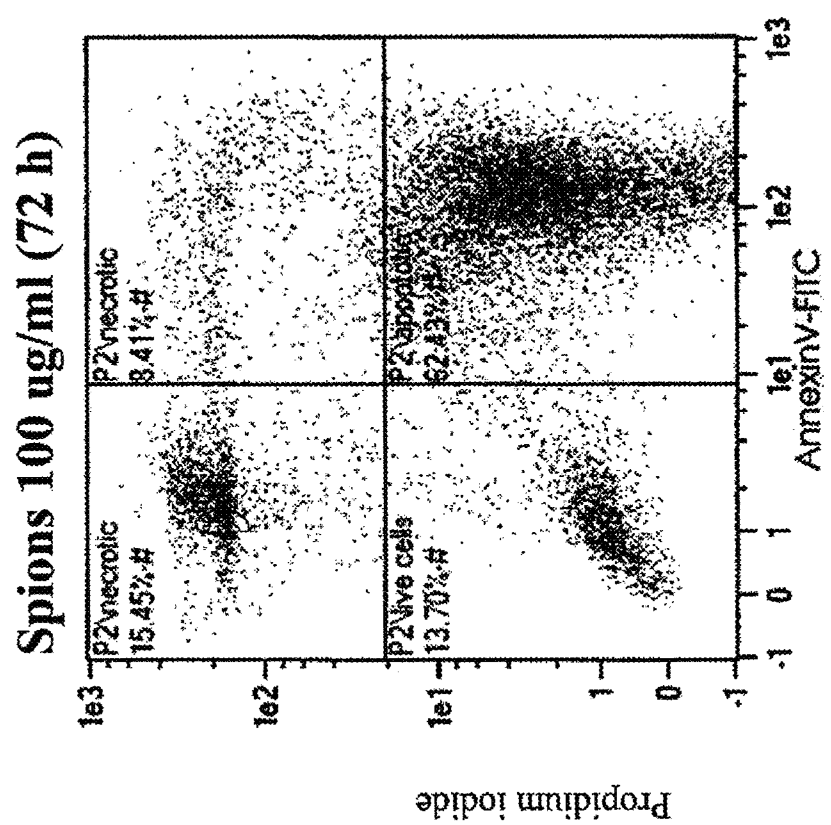
Figure 17C:
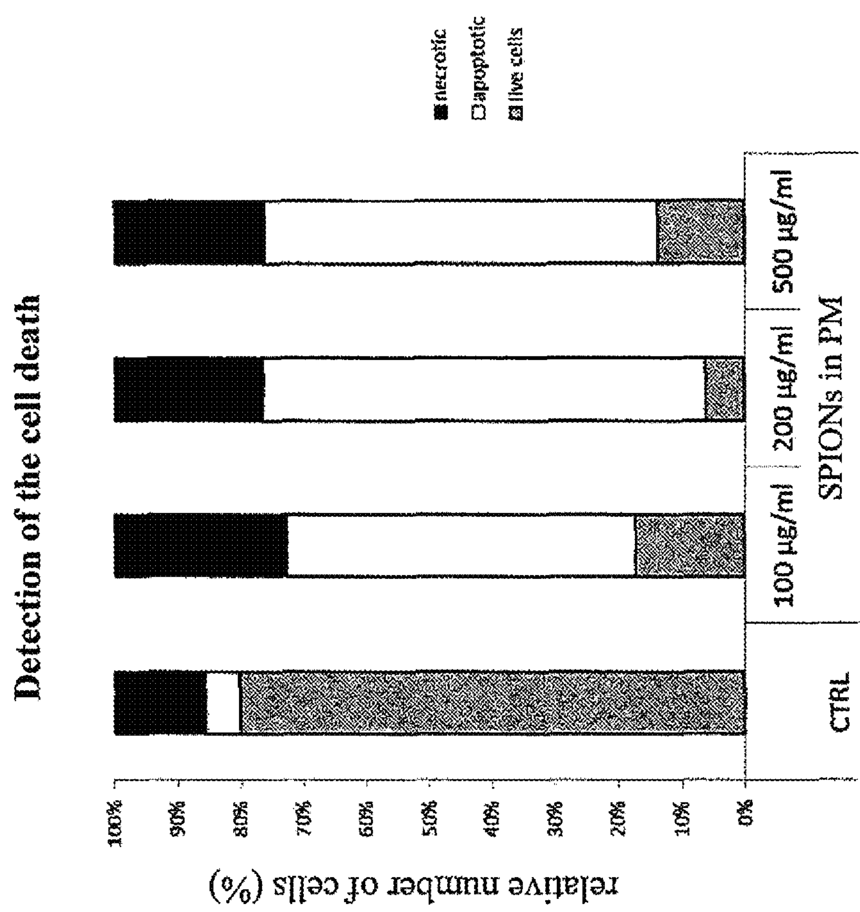

In FIGS. 17A-C, there is a clear induction of apoptosis (the cell population in the right lower quadrant, FIG. 17B) and a slightly increased induction of necrosis (left/right upper quadrant, FIG. 17B) after the treatment with a 100 μg/ml solution of the composition with SPIONs from Example 12. The representation of the live, apoptotic and necrotic cells after the treatment by the composition in the individual concentrations is plotted in the graph (FIG. 17C).

The invention claimed is:

1. An antitumor composition having a selective inhibitory effect on cancer cell growth, the composition based on a C18-acylated derivative of hyaluronic acid according to the general formula (I)

(I)

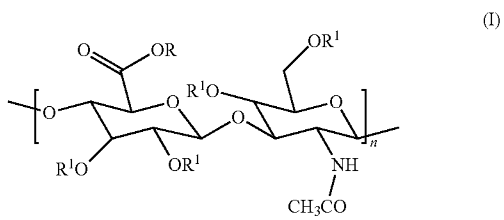

where R is $H^+$ or $Na^+$, and where $R^1$ is H or $—C(=O)C_{17}H_y$ or —C(=O)CH=CH-het, where y is an integer within the range of 29-35 and $C_{17}H_y$ is a linear or branched, saturated or unsaturated $C_{17}$ chain and het is a heterocyclic or heteroaromatic residue, optionally containing N, S or O atoms, wherein at least in one repeating unit one or more $R^1$ is $C(=O)C_{17}H_y$, and where n is within the range of 12 to 4000, and characterized in that the composition further contains superparamagnetic nanoparticles and a stabilizing oleic acid, such that the composition has a greater inhibitory effect on growth of cancer cells than on non-cancerous cells, and wherein the cancer cells are derived from colorectum carcinoma, adenocarcinoma, lung carcinoma, hepatocellular carcinoma, or breast adenocarcinoma, wherein the composition does not contain a cytostatic, and wherein the derivative of hyaluronic acid is in the form of nanomicelles having the superparamagnetic nanoparticles loaded therein.

2. The antitumor composition according to claim 1, characterized by that the acylated hyaluronan is a C18:1 acylated hyaluronic acid derivative.

3. The antitumor composition according to claim 1, wherein the superparamagnetic nanoparticles are based on iron oxides, where the amount of Fe in the composition is 0.3-3% wt.

4. The antitumor composition according to claim 1, wherein the superparamagnetic nanoparticles have a size of 5 to 20 nm.

5. The antitumor composition according to claim 1, wherein the superparamagnetic nanoparticles have a size of 5 to 7 nm.

6. The antitumor composition according to claim 1, wherein the superparamagnetic nanoparticles have a size of 5 nm.

7. The antitumor composition according to claim 1 for use in inhibition of growth of both adherent and suspension tumor cells.

8. The antitumor composition according to claim 1 for use in an in vivo detection of accumulation of the composition in the body.

9. The antitumor composition according to claim 1 for use in an in vivo detection of pathological formations in the body.

10. The antitumor composition according to claim 1, characterized by that it is applicable in a formulation for parenteral or local administration.

11. The antitumor composition according to claim 1, characterized by that it further contains other additives used in pharmaceutical compositions.

12. The antitumor composition of claim 11, wherein the additives are chosen from sodium chloride, dextrose, or buffering salts.

13. The antitumor composition according to claim 1, characterized by that it is sterilizable in a final casing by autoclaving.

14. A method of preparation of the composition defined in claim 1, characterized by that an aqueous solution of a C18-acylated derivative of hyaluronic acid according to the general formula (I) is prepared, then superparamagnetic nanoparticles dispersed in an organic halide solvent and stabilized by oleic acid are added, and the resulting suspension is sonicated until a homogenous mixture including nanomicelles is formed, and then the free superparamagnetic nanoparticles are separated from the superparamagnetic nanoparticles loaded in nanomicelles by centrifugation and a subsequent filtration.

15. The method according to claim 14, characterized by that the filtrate is subsequently lyophilized.

16. The method according to claim 15, characterized by that the lyophilizate is subsequently dissolved in an aqueous solution and sterilized by autoclaving in the final casing.

17. The method according to claim 14, characterized by that the filtrate is subsequently sterilized by autoclaving in the final casing.

18. The antitumor composition according to claim 1 for use in an in vivo detection of accumulation of the composition in a tumor and liver.

19. The antitumor composition according to claim 1 for use in an in vivo detection of pathological formations in tumors.

20. An antitumor composition consisting of:

a C18-acylated derivative of hyaluronic acid according to the general formula (I)

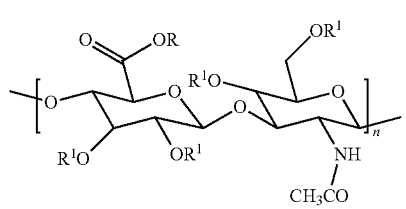

where R is $H^+$ or $Na^+$, and where $R^1$ is H or —C(=O)$C_{17}H_y$ or —C(=O)CH=CH-het, where y is an integer within the range of 29-35 and $C_{17}H_y$ is a linear or branched, saturated or unsaturated C17 chain and het is a heterocyclic or heteroaromatic residue, optionally containing N, S or O atoms, wherein at least in one repeating unit one or more $R^1$ is C(=O)$C_{17}H_y$, and where n is within the range of 12 to 4000;

superparamagnetic nanoparticles; and a stabilizing oleic acid;

wherein the composition has a selective inhibitory effect on cancer cell growth such that the composition has a greater inhibitory effect on growth of cancer cells than on non-cancerous cells.

21. An antitumor composition having a selective inhibitory effect on cancer cell growth, the composition based on a C18-acylated derivative of hyaluronic acid according to the general formula (I)

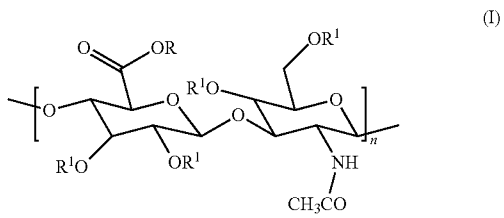

where R is $H^+$ or $Na^+$, and where $R^1$ is H or —C(=O)$C_{17}H_y$ or —C(=O)CH=CH-het, where y is an integer within the range of 29-35 and $C_{17}H_y$ is a linear or branched, saturated or unsaturated $C_{17}$ chain and het is a heterocyclic or heteroaromatic residue, optionally containing N, S or O atoms, wherein at least in one repeating unit one or more $R^1$ is C(=O)$C_{17}H_y$, and where n is within the range of 12 to 4000, and characterized in that the composition further contains superparamagnetic nanoparticles and a stabilizing oleic acid, such that the composition has a greater inhibitory effect on growth of cancer cells than on non-cancerous cells, and wherein the cancer cells are derived from colorectum carcinoma, adenocarcinoma, lung carcinoma, hepatocellular carcinoma, or breast adenocarcinoma, wherein the composition does not contain a cytostatic.

* * * * *

UNITED STATES PATENT AND TRADEMARK OFFICE

CERTIFICATE OF CORRECTION

PATENT NO. : 10,617,711 B2
APPLICATION NO. : 15/322776
DATED : April 14, 2020
INVENTOR(S) : Daniela Smejkalova et al.

It is certified that error appears in the above-identified patent and that said Letters Patent is hereby corrected as shown below:

On the Title Page

Item (56) Column 2, Page 3, Line 23, “Saccarides” should be --Saccharides--.

Item (56) Column 2, Page 4, Line 5, “modem” should be --modern--.

Item (56) Column 1, Page 5, Line 11, “Electrspun” should be --Electrospun--.

Item (56) Column 2, Page 9, Line 41, “filmis” should be --film is--.

In the Specification

Column 1, Line 47, “2001), As opposed to the” should be --2001). As opposed to the--.

Column 6, Line 18, “10 nm a 20 nm” should be --10 nm and 20 nm--.

Column 16, Line 15, “was monitored.” should be --were monitored.--.

Column 17, Line 44, “50.000” should be --50,000”--.

Column 19, Line 44, “Institut)” should be --Institute)--.

Signed and Sealed this
Sixteenth Day of June, 2020

Andrei Iancu
*Director of the United States Patent and Trademark Office*